United States Patent
Park

(10) Patent No.: US 9,763,813 B2
(45) Date of Patent: Sep. 19, 2017

(54) MEDICAL STENT

(71) Applicant: RBKPARK LLC, St. Charles, IL (US)

(72) Inventor: Richard Park, St. Charles, IL (US)

(73) Assignee: RBKPARK LLC, St. Charles, IL (US)

(*) Notice: Subject to any disclaimer, the term of this patent is extended or adjusted under 35 U.S.C. 154(b) by 0 days.

(21) Appl. No.: 14/984,033

(22) Filed: Dec. 30, 2015

(65) Prior Publication Data

US 2016/0106558 A1 Apr. 21, 2016

Related U.S. Application Data

(63) Continuation of application No. 12/614,228, filed on Nov. 6, 2009, now Pat. No. 9,233,012, which is a continuation-in-part of application No. 11/221,242, filed on Sep. 7, 2005, now Pat. No. 7,632,304.

(51) Int. Cl.
| | |
|---|---|
| A61F 2/06 | (2013.01) |
| A61F 2/856 | (2013.01) |
| A61F 2/82 | (2013.01) |
| A61F 2/844 | (2013.01) |
| A61F 2/88 | (2006.01) |
| A61F 2/91 | (2013.01) |

(52) U.S. Cl.
CPC ........... *A61F 2/856* (2013.01); *A61F 2/82* (2013.01); *A61F 2/844* (2013.01); *A61F 2/885* (2013.01); *A61F 2/91* (2013.01); *A61F 2002/826* (2013.01); *A61F 2250/0039* (2013.01); *A61F 2250/0067* (2013.01); *A61F 2250/0098* (2013.01)

(58) Field of Classification Search
CPC .... A61F 2/856; A61F 2002/821; A61F 2/852; A61F 2250/0096; A61F 2250/0097; A61F 2250/0098
USPC ....................................... 623/1.11, 1.34, 1.35
See application file for complete search history.

(56) References Cited

U.S. PATENT DOCUMENTS

| | | | |
|---|---|---|---|
| 5,725,572 | A | 3/1998 | Lam et al. |
| 5,746,766 | A | 5/1998 | Edoga |
| 6,203,568 | B1 | 3/2001 | Lombardi et al. |
| 6,231,598 | B1 | 5/2001 | Berry et al. |
| 6,582,394 | B1 | 6/2003 | Reiss et al. |
| 6,599,316 | B2 | 7/2003 | Vardi et al. |
| 6,749,528 | B2 | 6/2004 | Wengert |
| 6,749,628 | B1 | 6/2004 | Callol et al. |
| 6,896,699 | B2 | 5/2005 | Wilson et al. |
| 8,394,136 | B2 | 3/2013 | Hartley et al. |
| 9,233,012 | B2 * | 1/2016 | Park .......................... A61F 2/82 |
| 2001/0012961 | A1 | 8/2001 | Deem et al. |

(Continued)

OTHER PUBLICATIONS

Article from eMedicine, Percutaneous Transluminal Coronary Angioplasty, http://www.emedicine.com/med/topic3199.htm, Aug. 22, 2005.

(Continued)

*Primary Examiner* — Katherine Rodjom

(74) *Attorney, Agent, or Firm* — Banner & Witcoff, Ltd.

(57) ABSTRACT

In an embodiment, a stent is provided for use in blood vessels with blockage near or in a bifurcation. The stent includes a side aperture. The stent is inserted into one of the daughter branches of the bifurcation and positioned with the use of markers. The stent is then expanded so as to support the wall of the blood vessel while allowing the blood to continue to flow to both daughter branches.

19 Claims, 24 Drawing Sheets

(56) References Cited

U.S. PATENT DOCUMENTS

| | | |
|---|---|---|
| 2005/0060028 A1 | 3/2005 | Horres et al. |
| 2005/0113686 A1 | 5/2005 | Peckham |
| 2005/0131518 A1 | 6/2005 | Hartley et al. |
| 2006/0106455 A1 | 5/2006 | Furst et al. |
| 2006/0253186 A1 | 11/2006 | Bates |
| 2006/0287712 A1 | 12/2006 | Eidenschink |

OTHER PUBLICATIONS

Article from Journal of the American College of Cardiology, Aug. 16, 2005, vol. 46, No. 4, Revascularization in Severe Left Ventricular Dysfunction: The Role of Viability Testing, Chareonthaitawee, et al., p. 567.

Article from Journal of the American College of Cardiology, Aug. 16, 2005, vol. 46, No. 4, Five-Year Outcomes After Coronary Stenting Versus Bypass Surgery for the Treatment of Multivessel Disease: The Final Analysis of the Arterial Revascularization Therapies Study (AETS) Randomized Trial, Serruys, et al., p. 575.

Article from Journal of the American College of Cardiology, Aug. 16, 2005, vol. 46, No. 4, Five-Year Follow-Up of the Argentine Randomized Trial of Coronary Angioplasty With Stenting Versus Coronary Bypass Surgery in Patients With Multiple Vessel Disease (ERACI II), Rodriquez, et al., p. 582.

Article from Journal of the American College of Cardiology, Aug. 16, 2005, vol. 46, No. 4, Stenting or Surgery: An Opportunity to Do It Right, Robert M. Califf, M.D., FACC, p. 589.

Article from Journal of the American College of Cardiology, Aug. 16, 2005, vol. 46, No. 4, The FRONTIER Stent Registry: Safety and Feasibility of a Novel Dedicated Stent for the Treatment of Bifurcation Coronary Artery Lesions, Lefevre, et al., p. 592.

Article from Journal of the American College of Cardiology, Aug. 16, 2005, vol. 46, No. 4, Bifurcation Coronary Lesions Treated With the "Crush" Technique, An Intravascular Ultrasound Analysis, Costa, et al., p. 599.

Article from Journal of the American College of Cardiology, Aug. 16, 2005, vol. 46, No. 4, Nine-Month Outcome of Patients Treated by Percutaneous Coronary Interventions for Bifurcation Lesions in the Recent Era: A report From the Prevention of Restenosis With Tranilast and its Outcomes (PRESTO) Trial; Garot, et al., p. 606.

Article from Journal of the American College of Cardiology, Aug. 16, 2005, vol. 46, No. 4, Clinical and Angiographic Outcome After Implantation of Drug-Eluting Stents in Bifurcation Lesions With the Crush Stent Technique, Importance of Final Kissing Balloon Post-Dilation, Ge, et al., p. 613.

Article from Journal of the American College of Cardiology, Aug. 16, 2005, vol. 46, No. 4, Bifurcation Intervention: Is it Crush Time Yet? Williams, et al., p. 621.

Article from Journal of the American College of Cardiology, Aug. 16, 2005, vol. 46, No. 4,Relationship Between Operator Volume and Adverse Outcome in Contemporary Percutaneous Coronary Intervention Practice: An Analysis of a Quality-Controlled Multicenter Percutaneous Coronary Intervention Clinical Database, Moscucci, et al., p. 625.

Article from Journal of the American College of Cardiology, Aug. 16, 2005, vol. 46, No. 4, Physiologic Assessment of Jailed Side Branch Lesions Using Fractional Flow Reserve, Koo, et al., p. 633.

Article from Journal of the American College of Cardiology, Aug. 16, 2005, vol. 46, No. 4, Matching the Evaluation of the Clinical Efficacy of Clopidogrel to Platelet Function Tests Relevant to the Biological Properties of the Drug, Labarthe, et al., p. 638.

Article from Journal of the American College of Cardiology, Aug. 16, 2005, vol. 46, No. 4, Clopidogrel: Linking Evaluation of Platelet Response Variability to Mechanism of Action, Frelinger, et al., p. 646.

Article from Journal of the American College of Cardiology, Aug. 16, 2005, vol. 46, No. 4, Endothelial Vasomotor Dysfunction in the Brachial Artery is Associated With Late In-Stent Coronary Restenosis, Kitta, et al., p. 648.

Article from Journal of the American College of Cardiology, Aug. 16, 2005, vol. 46, No. 4, Impaired Endothelial Function in Coronary Heart Disease Patients With Depressive Symptomatology, Sherwood, et al., p. 656.

Article from Journal of the American College of Cardiology, Aug. 16, 2005, vol. 46, No. 4,The Economic Effect of a Tertiary Hospital-Based Heart Failure Program, Gregory, et al., p. 660.

Article from Journal of the American College of Cardiology, Aug. 16, 2005, vol. 46, No. 4,Electrogram characteristics in Postinfarction Ventricular Tachycardia: Effect of Infarct Age, Bogun, et al., p. 667.

Article from Journal of the American College of Cardiology, Aug. 16, 2005, vol. 46, No. 4, "The Older the Broader": Electrogram Characteristics Help Identify the Critical Isthmus During Catheter Ablation of Postinfarct Ventricular Tachycardia, Klein, et al., p. 675.

Article from Journal of the American College of Cardiology, Aug. 16, 2005, vol. 46, No. 4, The Combined Use of Ibutilide as an Active Control With Intensive Electrocardiographic Sampling and Signal Averaging as a Sensitive Method to Assess the Effects of Tadalafil on the Human QT Interval, Beasley, Jr. et al., p. 678.

Article from Journal of the American College of Cardiology, Aug. 16, 2005, vol. 46, No. 4, Making a Silk Purse Out of a Sow's Ear, Kowey, et al., p. 688.

Article from Journal of the American College of Cardiology, Aug. 16, 2005, vol. 46, No. 4, Prevalence and Clinical Significance of Left Atrial Remodeling in Competitive Athletes, Pelliccia, et al., p. 690.

Article from Journal of the American College of Cardiology, Aug. 16, 2005, vol. 46, No. 4, Effects of Long-Term Bosentan in Children With Pulmonary Arterial Hypertension, Rosenzweig, et al., p. 697.

Article from Journal of the American College of Cardiology, Aug. 16, 2005, vol. 46, No. 4, Improving the Outcome of Childhood Pulmonary Arterial Hypertension: The Effect of Bosentan in the Setting of a Dedicated Pulmonary Hypertension Clinic, Ian Adatia, MBCHB, p. 705.

Article from Journal of the American College of Cardiology, Aug. 16, 2005, vol. 46, No. 4, Plasma Tissue Factor Plus Activated Peripheral Mononuclear Cells Activate Factors VII and X in the Cardiac Surgical Wounds, Hattori, et al. p. 707.

Article from Journal of the American College of Cardiology, Aug. 16, 2005, vol. 46, No. 4, Thickening of the Infarcted Wall by Collagen Injections Improves Left Ventricular Function in Rats: A Novel Approach to Preserve cardiac Function After Myocardial Infarction, Dai, et al., p. 714.

Article from Journal of the American College of Cardiology, Aug. 16, 2005, vol. 46, No. 4, Functional and Morphologic Imaging of Coronary Atherosclerosis in Living Mice Using High-Resolution Color Doppler Echocardiography and Ultrasound Biomiropscopy, Wikström, et al., p. 720.

Article from Journal of the American College of Cardiology, Aug. 16, 2005, vol. 46, No. 4, The Department of Cardiac/Vascular Medicine and Surgery, Anthony N. DeMaria, MD, MACC, p. 728.

Article from Journal of the American College of Cardiology, Aug. 16, 2005, vol. 46, No. 4, Research Correspondence, Risk Stratification of Patients With Classic Angina Pectoris and No History of Coronary Artery Disease by Dobutamine Stress Echocardiography, Biagini, et al., p. 730.

International Search Report in related International Patent Application No. PCT/US06/34411, pp. 1-9, Sep. 25, 2007.

Schneller et al., "Contrast Media as Carriers for Local Drug Delivery Successful Inhibition of ; Neointimal Proliferation in the Porcine Coronary Stent Model", European Heart Journal (2003) 24, 1462-1467: ; p. 1466, para. 2 and 5-6.

* cited by examiner

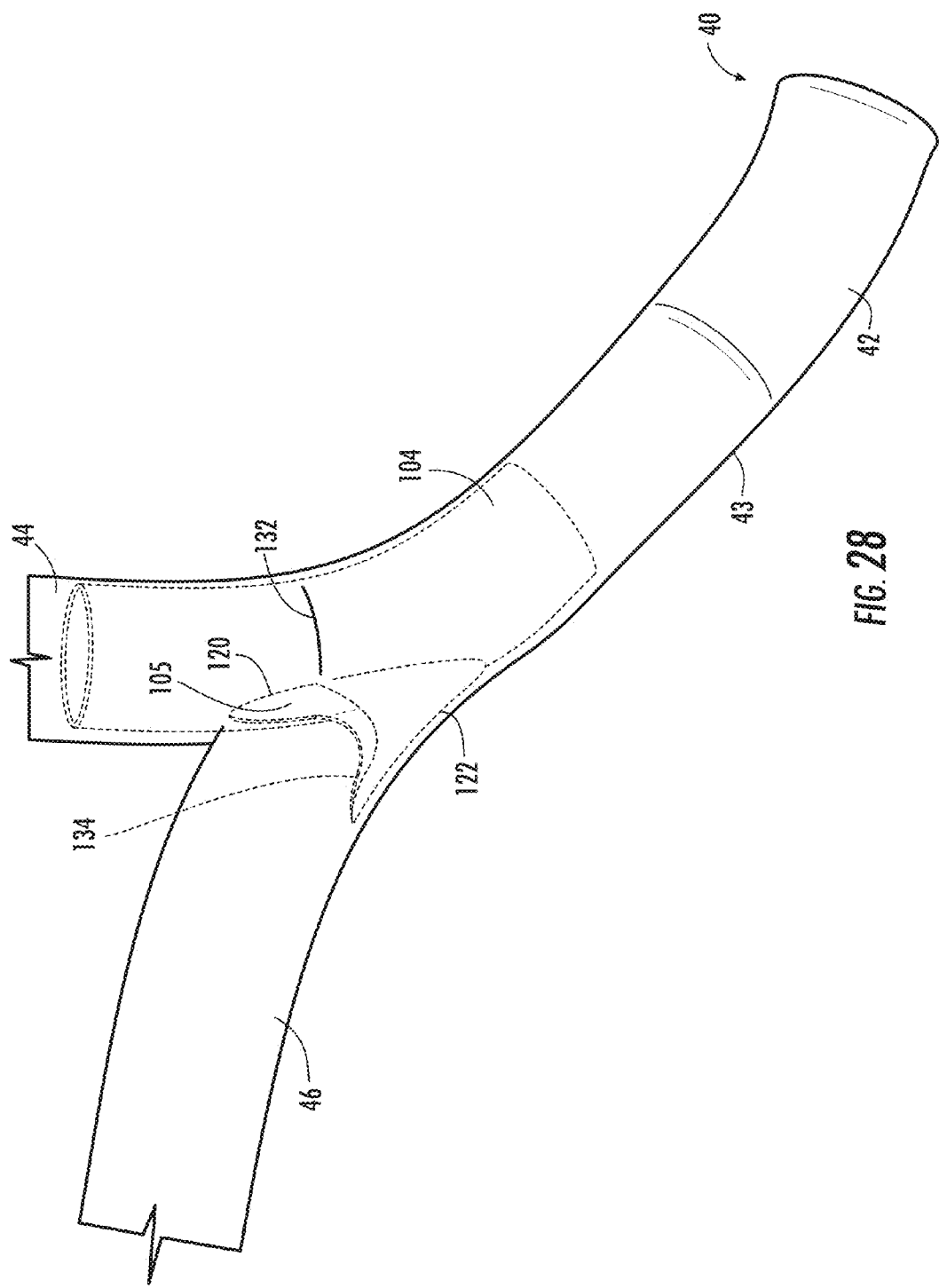

MEDICAL STENT

CROSS REFERENCE TO RELATED APPLICATIONS

This application is a continuation of U.S. patent application Ser. No. 12/614,228, filed Nov. 6, 2009, which is a continuation-in-part application of U.S. patent application Ser. No. 11/221,242, filed Sep. 7, 2005, now U.S. Pat. No. 7,632,304, the disclosure of which is hereby incorporated by reference in its entirety.

FIELD OF THE INVENTION

The present invention relates to the field of medical devices, more specifically to the field of implantable stents.

DESCRIPTION OF RELATED ART

As is known, the human heart circulates blood throughout the body. Depending on the individual, the heart beats between 80,000 and 140,000 times per day. During normal function of the heart, the left and right atria and the left and right ventricles contract, causing blood to flow. The blood flows from the heart, passes through a set of blood vessels known as arteries that feed the organs and tissue in the body and then returns to the heart through a set of blood vessels known as veins. This circulation provides nutrients and oxygen to the body so that it can continue to function.

As the heart is basically a continuously functioning muscle, it also needs a steady supply of nutrients in order to function. For example, a coronary artery supplies blood (and the associated oxygen and nutrients) to the cardiac muscle. In order for the heart to continue to function, it is crucial that this artery continue to function properly.

Unfortunately, the coronary artery can become partially or completely blocked. One cause is left main coronary artery disease ("LMCD"). LMCD may be caused, for example, by the accumulation of fatty tissue on the wall of the left main artery. LMCD is generally defined as a greater than 50% reduction in the left main, which results in insufficient blood flow to the heart tissue and eventually causes damage to the heart tissue.

While partial blockage can result in permanent damage to the heart muscle, sudden complete blockage of the left main will result in the death of the individual. Therefore, maintaining blood flow through the left main is crucial to an individual's ability to exist. Any symptomatic blockage must be immediately treated.

Two methods of treatment of a partially or completely blocked left main are 1) percutaneous transluminal coronary angioplasty ("PTCA"), also referred to as percutaneous coronary intervention ("PCI"), and commonly referred to as balloon angioplasty or angioplasty, and 2) coronary artery bypass graft ("CABG"), commonly referred to as bypass surgery. Due to a number of factors, the most common procedure to treat LMCD has been bypass surgery.

In essence, bypass surgery uses section of veins or arteries sections from other parts of the body to connect the aorta to a point downstream of the blockage. This allows blood to flow around the blockage point through a separate passageway. Depending on the severity and location of the blockage, as many as four to five grafts are necessary.

One downside to bypass surgery is that it takes a substantial time to perform. For a patient with a totally occlusion or a severely blocked left main, the time it takes to perform bypass surgery may be too long. Therefore, in emergencies, balloon angioplasty has been performed on patients suffering from sudden LMCD.

Another problem is that bypass surgery is only effective for about 8-10 years, at which point a patient generally requires additional treatment that is generally less effective. Given the potential long-term health problems, it is desirable to delay bypass surgery if possible.

Furthermore, certain patients' medical conditions are incompatible with the rigors of bypass surgery. For example, some patients have severe co-morbid conditions precluding open-heart surgery, such as malignancy with limited life-expectancy, no longer are a candidate for bypass surgery. Thus, while bypass surgery is a useful medical procedure that has saved many lives, it is best saved for situations where less complex procedures cannot be used effectively.

In addition, some interventional cardiac catheterization labs are not backed up by surgical programs. This is problematic in situations where the LMCD must be treated immediately (e.g. iatrogenic dissection of the left main).

Compared to bypass surgery, angioplasty can be done relatively quickly and is generally less traumatic to the patient. Basically, during angioplasty a wire is inserted into the artery. A flexible catheter is then guided along the wire. A balloon attached to the catheter is positioned in the left main at the point of blockage and the balloon is inflated to open the artery. To keep the artery open, a stent may be placed in the left main. One common method of delivering the stent is to wrap it around the balloon. Thus, the inflation of the balloon causes the stent to expand into position. The stent acts as a scaffolding to support the wall of the artery and, when coated with anti-restenotic agents, can be an alternative means of treating certain types of LMCD.

While the expansion of blocked portions of arteries with angioplasty can be effective, certain areas of the left main have proven difficult to treat with balloon angioplasty. Sometimes the blockage occurs at a point of junction between the left main and the left anterior descending artery and the left circumflex artery. In such a situation, expansion and insertion of a stent into one of the secondary branches has the tendency to jeopardize the other branch.

Attempts have been made to provide a customized stent that can be used in a junction to support the main branch and the two secondary branches but such an approach has limitations. For one thing, the secondary branches and angles between the different branches are varied from person to person as well as from junction to junction, making it difficult to design a single stent that can work with all the potential variations. Furthermore, such a design is difficult to install, thus making it less attractive to locations such as the junction in the left main. Another major limitation is that much higher operator skill is required to position such a stent quickly, thus making it more likely that such a stent will be improperly installed. Therefore, often the only choice is to attempt bypass surgery. However, in the face of complete blockage it is possible that a patient will not survive the procedure. Clearly, something more is needed to address such a life-threatening emergency. In addition, it would be beneficial to provide a stent that could be used in and near the left main junction during more routine medical situations as an alternative to bypass surgery. Further, other medical fields would greatly benefit from improved stents and methods for implanting stents.

Furthermore, in certain medical procedures, two or more stents are often implanted in close proximity to each other. In certain instances, it is highly desirable to join two stents in a parallel-like fashion. Because of individual variation and other factors, it is often too difficult to precisely join two or more stents. Problems associated with this are described in more detail below in relation to FIG. 29. Reducing or eliminating problems often associated with joining two or more stents would be beneficial to several medical fields.

BRIEF SUMMARY OF THE INVENTION

Aspects of the invention relate to medical stents and methods for implanting medical stents. One aspect relates to novel stents that include at least one extension extending in a substantially continuous form from the stent. In one embodiment, the extension extends from a portion of an aperture on a side of the stent. The extension may be present over the perimeter of the aperture, for example, forming a hood-like protrusion that arches over the perimeter. In one embodiment, the extension extends at least about 25-30% around the perimeter. In other embodiment, the extension extends less than about 50% of the perimeter. In one embodiment, the extension extends about 100% around the perimeter, however, has a shorter length on one side extending from the aperture than another side extending from the aperture.

The extension may be configured to be in a collapsed state and, upon expansion of the stent, may be configured to flex outward from the main body of the stent. In certain embodiments, one or more markers may be positioned on a cylindrical body of the stent and/or the extension. In one embodiment, a first marker may be positioned in-line with and directly extending from the location where the distance of the aperture along the latitudinal direction is the greatest. The first marker may be configured to provide a rotation orientation of the stent in a dimensional image. In another embodiment, a marker may be positioned on the extension. In one embodiment, the marker arches in a latitudinal direction over the perimeter of the aperture in a direction that is substantially perpendicular to a longitudinal axis of the stent so as to provide a rotation orientation of the extension in a dimensional image. One such marker may create an arch across the furthest point away from the aperture. The marker may be directly aligned with a centerline of the side aperture. One marker may be positioned parallel with the longitudinal axis of the cylinder wall of the stent. In embodiments with two or more markers, a first marker and a second marker may be configured so as to appear substantially perpendicular to each other in a two dimensional image and the second marker is positioned adjacent the side aperture and extends a distance at least equal to a greatest longitudinal distance of the side aperture.

Certain aspects of the invention relate to methods relating to medical stents. In one embodiment, an exemplary method is directed towards supporting a wall in a junction, such as of a blood vessel. A method according to certain embodiments may be implemented in a junction having a main branch that extends to a first branch and a second branch, although additional branches are within the scope of further embodiments. In one embodiment, a stent with a side aperture may be positioned in the junction. In one method, a stent is implanted in which the extension arches in a latitudinal direction over the perimeter of the aperture in a direction that is substantially perpendicular to a longitudinal axis. Yet, in further embodiments, the extension may arch along any direction.

Certain methods may utilize a stent with one or more markers. In one embodiment, the stent may have a marker aligned with the side aperture at a location where a distance of the aperture along the latitudinal direction is the greatest. The marker may extend along a circumference of the stent a distance substantially perpendicular to a longitudinal axis of the stent as to, in accordance with certain embodiments, provide a rotational orientation of the stent in a dimensional image. In one embodiment, the method is configured to allow the implantation of a stent with a marker that creates an arch across the furthest point away from the aperture. In another embodiment, two or more markers may configured so as to appear substantially perpendicular to each other in a two dimensional image. The marker may be positioned adjacent to the side aperture and extends a distance at least equal to a greatest longitudinal distance of the side aperture.

Certain methods may expand the stent so as to support the wall of the main branch and the first branch, whereby the side aperture allows the main branch to continue to feed both the first and the second branch. The stent may include an extension, which in accordance with one or more embodiments, be expanded to extend in a substantially continuous form from a portion of the side aperture's perimeter. In one embodiment, the extension may flex outward from the cylinder wall form a protrusion that arches in a latitudinal direction over the perimeter and extends into the second branch. The expansion of the stent may be a result of the expansion of the stent. In one embodiment, the expansion of the extension occurs after the expansion of the stent.

Further embodiments may include the insertion of a guide wire. In such embodiments, a balloon may be positioned over the guide wire and into a bifurcation of the branch with the stent positioned on the outside of the balloon. In one embodiment, a portion of a stent may be inserted into a first branch and a marker may be aligning the marker with the second branch. In one embodiment, the stent with a side aperture is inserted into a junction of a left main coronary artery that includes a main branch and two secondary branches so that the side aperture aligns with one of the secondary branches while the stent extends into the other secondary branch. In one embodiment, a stent may be expanded so as to support a wall of the left main coronary artery while allowing blood to flow through the side aperture into one of the secondary branches. In certain embodiment, the stent (including the extension) may be coated with a pharmaceutical agent.

BRIEF DESCRIPTION OF THE DRAWINGS

The present invention is illustrated by way of example and not limited in the accompanying figures in which like reference numerals indicate similar elements and in which:

FIG. 25 shows an exemplary stent with an extension in accordance with one embodiment of the invention. Specifically.

FIG. 26 shows an exemplary stent with an extension in accordance with one embodiment of the invention. Specifically.

FIG. 28 shows a perspective view of an exemplary stent with an extension in accordance with one embodiment of the invention.

FIG. 29 shows a support structure created by two stents. Specifically.

FIG. 30 shows an exemplary stent with an extension in accordance with one embodiment of the invention. Specifically.

FIG. 31 shows an exemplary stent with an extension in accordance with one embodiment of the invention. Specifically.

DETAILED DESCRIPTION OF THE INVENTION

The description below will discuss various medical conditions and how a stent may be used to aid in the treatment these medical conditions. It is noted that the methods and apparatus disclosed are not limited to the treatment of the medical conditions disclosed but may be used to treat other medical conditions where appropriate.

Figure 1:
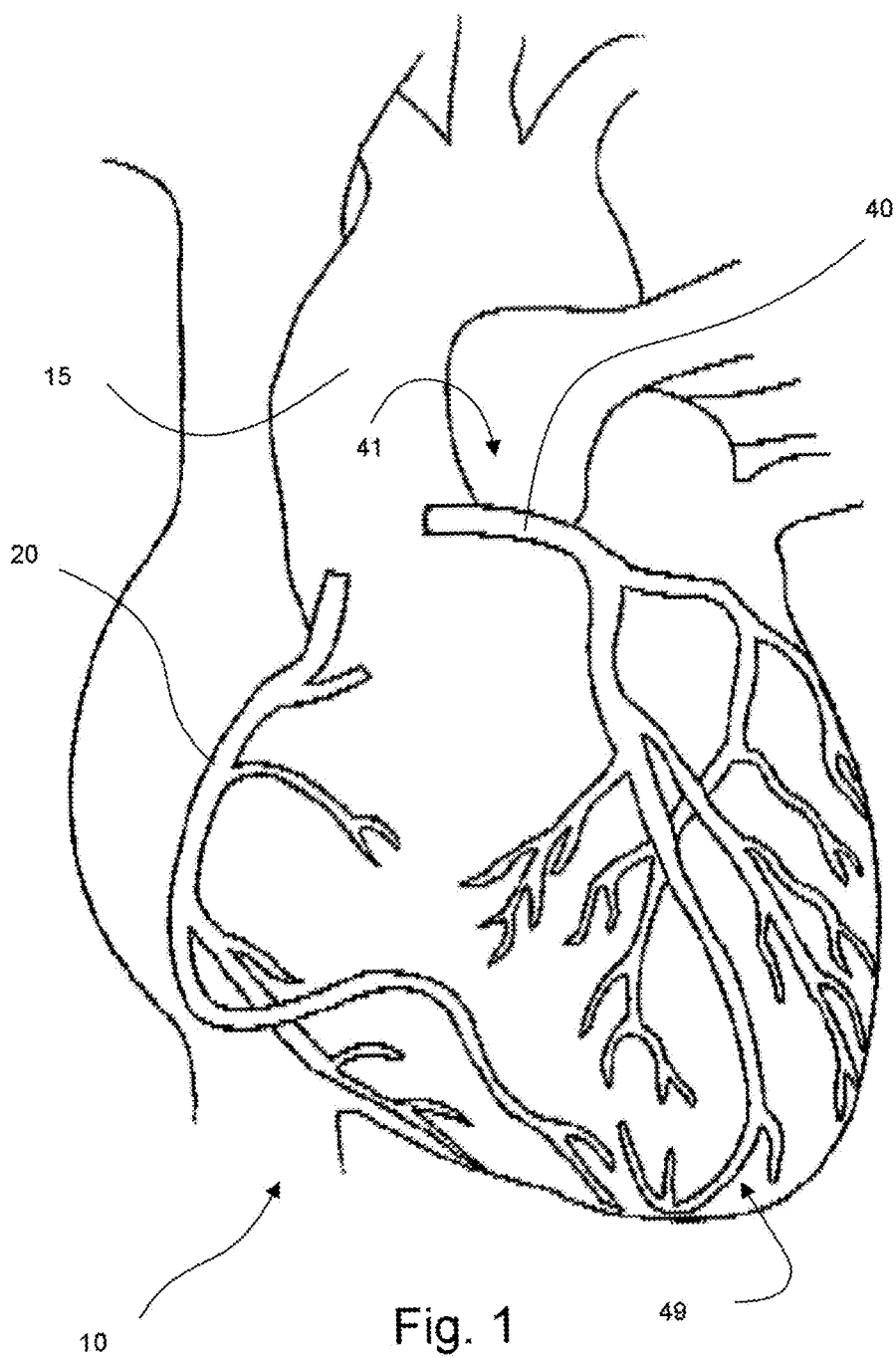
FIG. 1 illustrates an embodiment of a human heart.

Looking first at FIG. 1, an embodiment of a heart 10 is depicted. The heart 10 is fed by a right coronary artery 20 that branches out and provides blood to a portion of the heart. A left coronary artery 40 is also shown and also branches out and provides blood to a portion of the heart. As can be appreciated, a blockage at the beginning or proximal end 41 of the left coronary artery 40 would affect the flow of blood to all points downstream while a blockage at the distal end 49 of the left coronary artery 40 might have little or no discernable effect on the viability of the heart 10.

Figure 2:
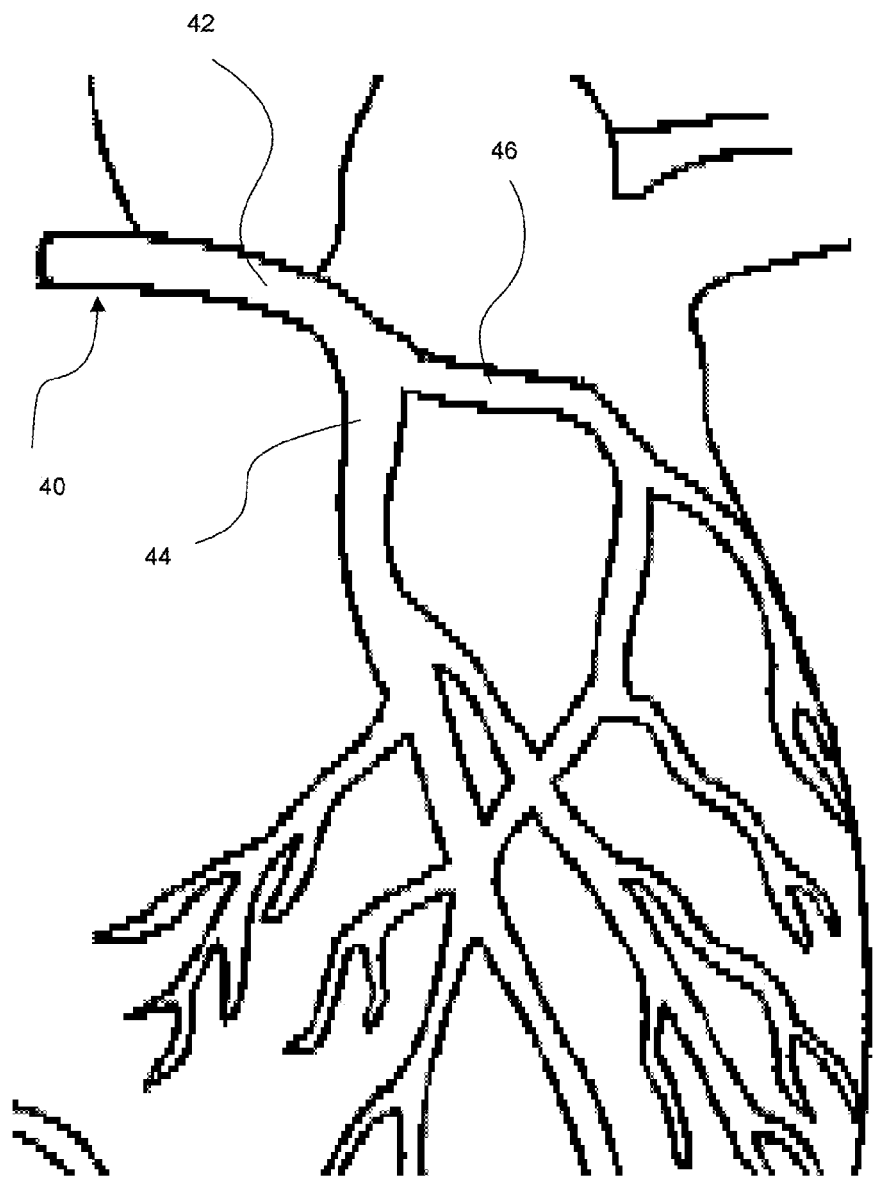
FIG. 2 illustrates an enlarged view of the human heart in FIG. 1, illustrating the left main coronary artery.

Turning to FIG. 2, the left coronary artery 40 is shown in an enlarged view that includes the left main artery or main branch 42 that feeds a first branch 44 (which as depicted is the left anterior descending artery) and a second branch 46 (which as depicted is the left circumflex artery).

Figure 3:
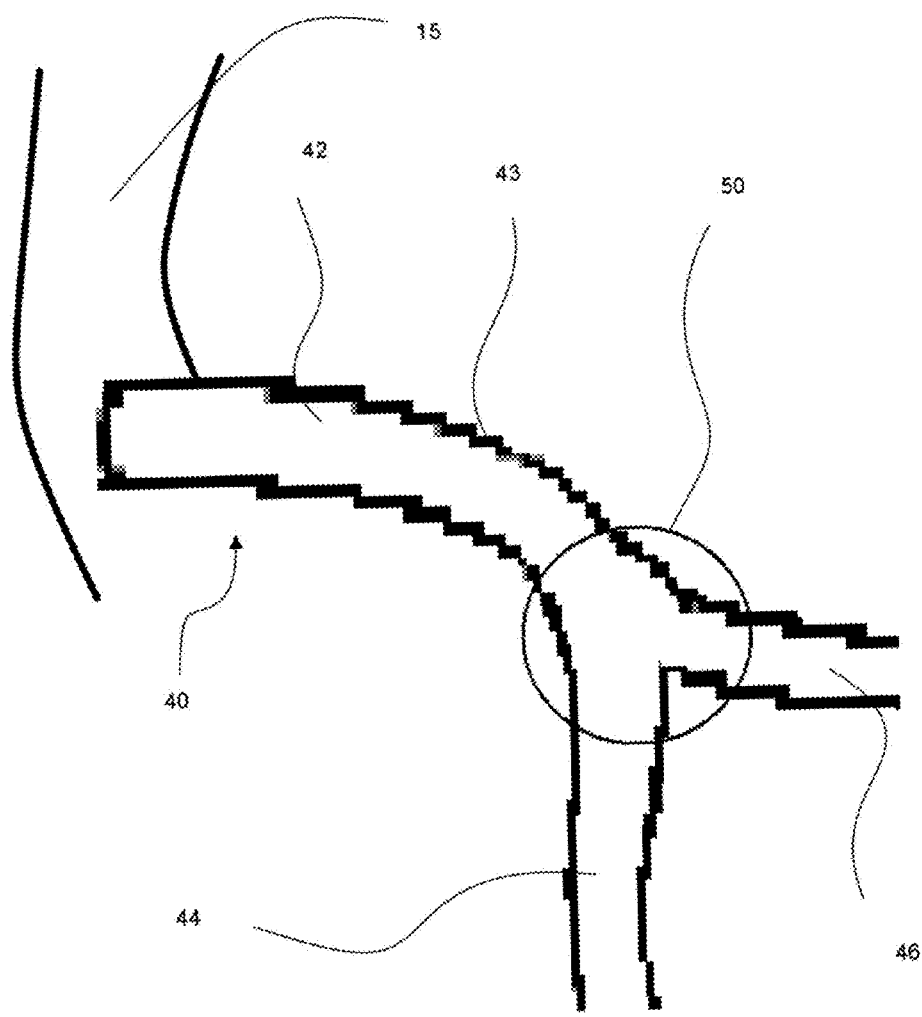
FIG. 3 illustrates a further enlarged view of the left main coronary artery of the human heart depicted in FIG. 2.

As depicted in FIG. 3, the first branch 44 shows a further enlarged view of the left coronary artery 40. The main branch 42 forms a junction 50 where it bifurcates into the first branch 44 and the second branch 46. As can be further appreciated, the main branch 42 includes a wall 43. In order for blood to flow through the left coronary artery 40, the wall 43 forms a tube-like shape that preferably is free from blockage.

Figure 4:
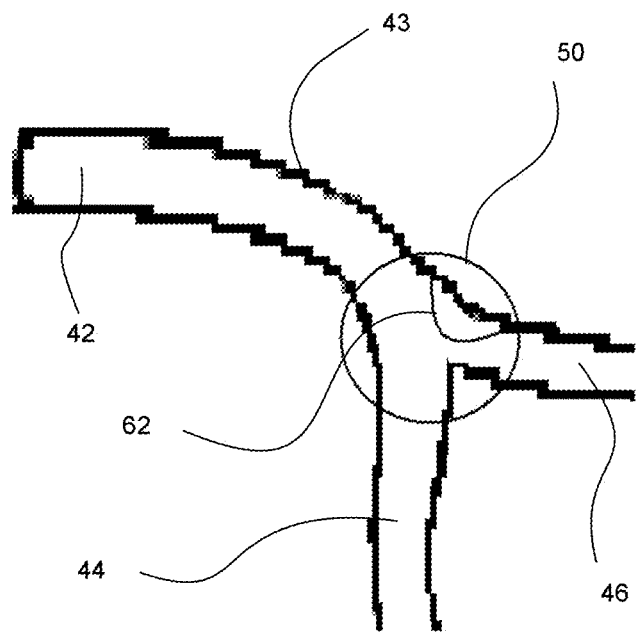
FIG. 4 illustrates an embodiment of blockage in an artery of a human heart in accordance with an aspect of the present invention.
Figure 5:
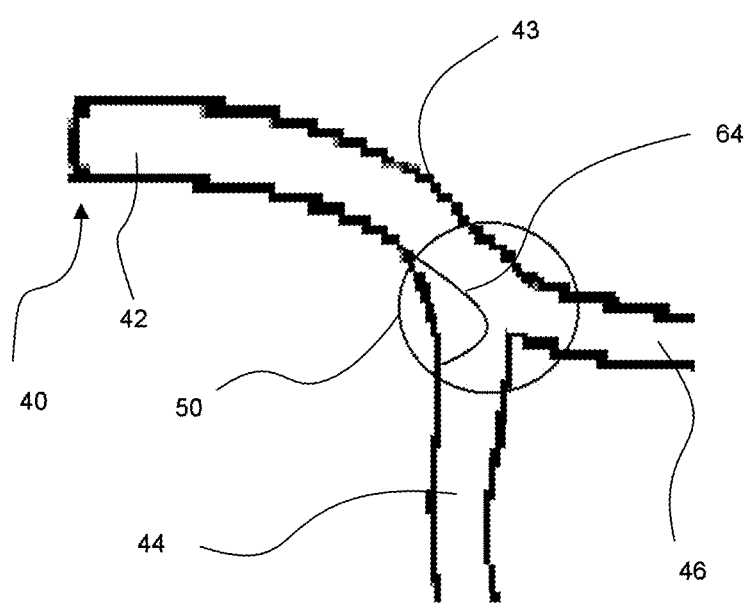
FIG. 5 illustrates an alternative embodiment of blockage in an artery of a human heart in accordance with an aspect of the present invention.

Unfortunately, as shown in FIG. 4, a blockage 62 may be formed by, for example, deposits of fatty tissue on the wall 43 in the junction 50. In FIG. 4, the blockage 62 partially occludes the flow of blood into the second branch 46. FIG. 5 depicts a similar situation except that the blockage 64 partially occludes the first branch 44.

Figure 6A:
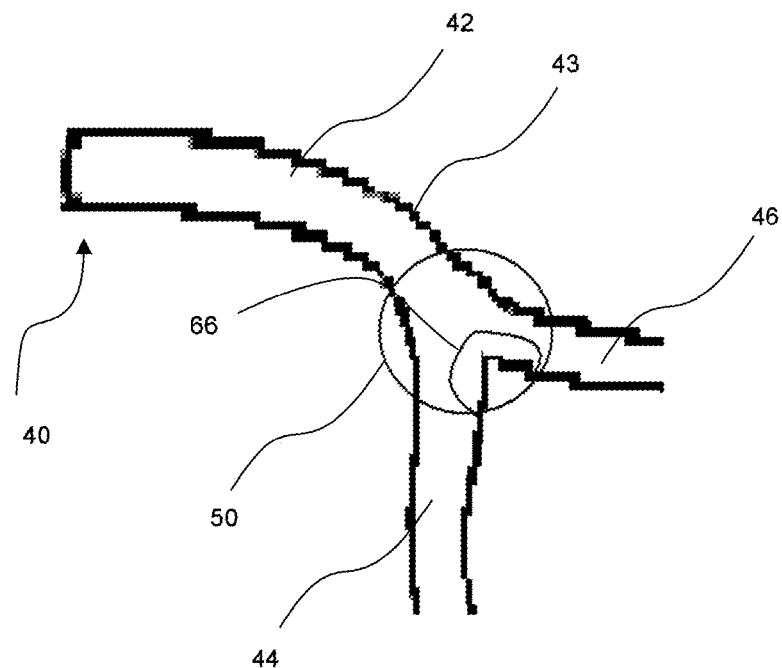
FIG. 6a illustrates an alternative embodiment of blockage in an artery of a human heart in accordance with an aspect of the present invention.
Figure 6B:
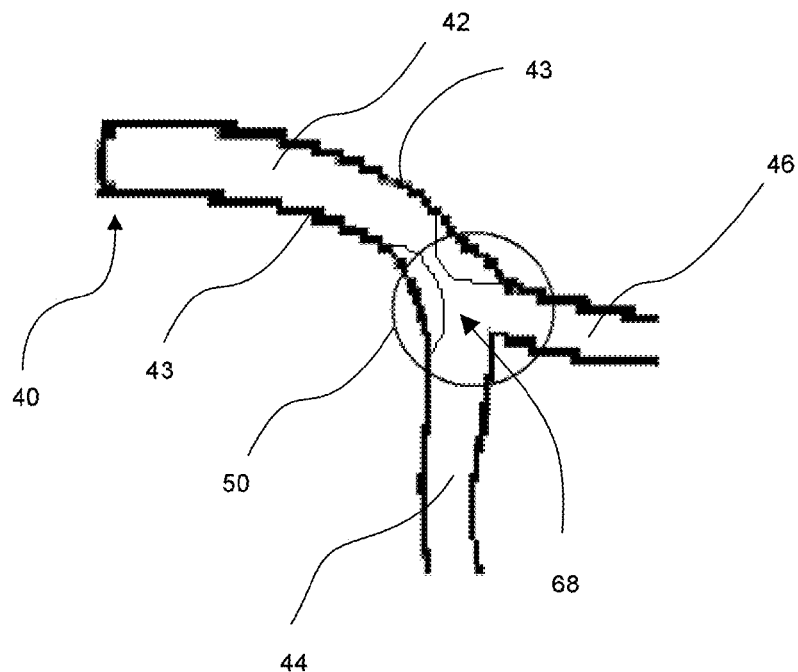
FIG. 6b illustrates an alternative embodiment of blockage in an artery of a human heart in accordance with an aspect of the present invention.

FIG. 6a illustrates a blockage 66 in the junction 50 that occludes blood flow to both the branch 44 and the branch 46. FIG. 6b illustrates a blockage 68 that is not within the junction 50 but affects blood flow to the first branch 44 and the second branch 46. As can be appreciated by FIGS. 4-6b, blockage in or near the junction 50 tends to require a solution that allows blood to flow to both branches 44, 46. It is noted that numerous other configurations of blockage near or in the junction 50 are possible. In an embodiment the blockage will occlude the main branch; in alternative embodiments the first branch or the second branch or a combination of two or more branches will be occluded by the blockage.

Figure 7:
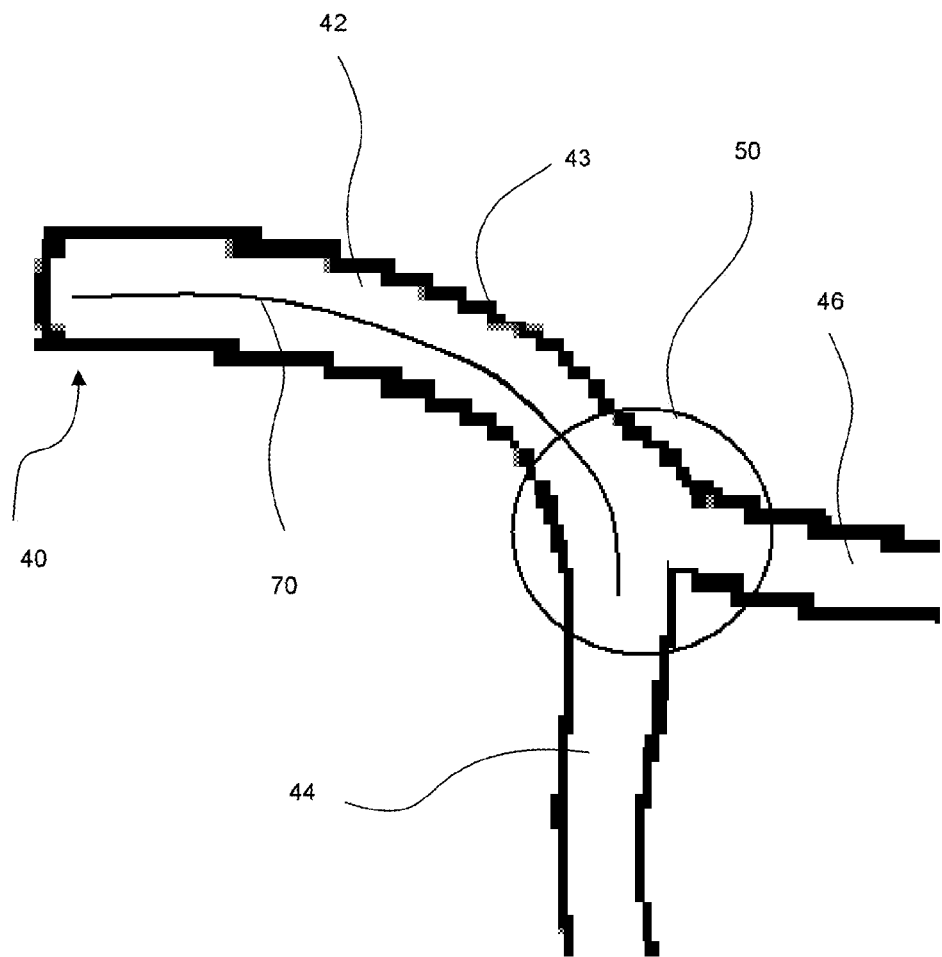
FIG. 7 illustrates an embodiment of a guide wire being inserted into coronary in accordance with an aspect of the present invention.

Turning to FIG. 7, an illustration of the left coronary artery 40 without any blockage depicted is provided, the blockage being omitted for the sake of clarity. In an embodiment a guide wire 70 may be inserted into the left coronary artery 40 in a known manner. As depicted, the guide wire 70 is inserted into the junction 50 and extends into the first branch 44. As can be appreciated, the distance the guide wire 70 extends into the junction 50 may be adjusted depending on the location of the blockage.

Figure 8:
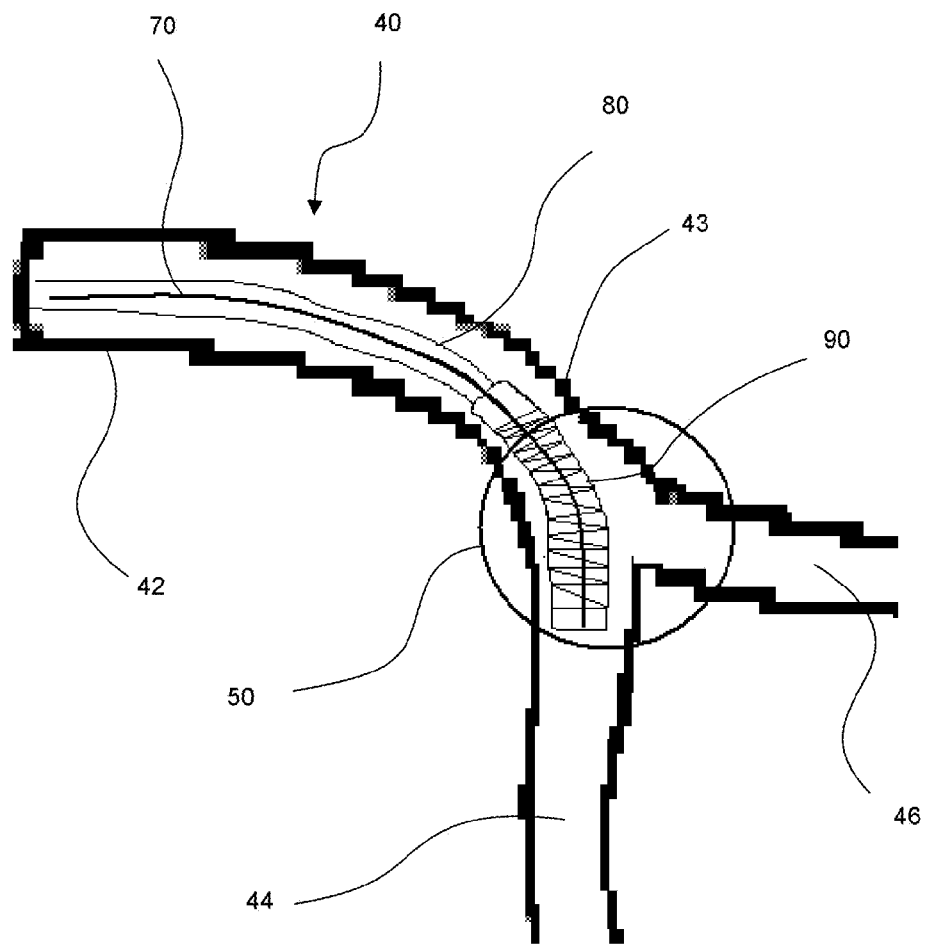
FIG. 8 illustrates an embodiment of an angioplasty balloon being inserted into coronary in accordance with an aspect of the present invention.

Turning to FIG. 8, after the guide wire is inserted, the next step is to guide a catheter 80 connected to an angioplasty balloon ("balloon") 90 along the guide wire into the desired position. Once the balloon 90 is correctly positioned, the balloon 90 is inflated so as to open up the portion of the left coronary artery 40 that was stenosed by the blockage. To help keep the left main open, the balloon 90 includes a stent 100 (not shown in FIG. 8) mounted on the exterior of the balloon 90. When the balloon 90 is expanded to open up the passageway, the stent 100 is also expanded. Once the passageway is opened, the pressure inflating the balloon 90 is removed and the balloon 90 contracts. However, the stent 100 remains in position so as to provide support for the wall 43 of the left coronary artery 40.

It should be noted that the balloon 90 may be compliant or non-compliant, depending on the intended use. Generally speaking, balloons that are non-complaint have a fixed amount of expansion and do not effectively increase in diameter in response to increases in internal pressure. In contrast, balloons that are compliant do effectively increase in diameter in response to increases in internal pressure. The balloon 90 may also be semi-compliant and thus provide some minimal amount of expansion in response to greater pressure. While different levels of compliance may be suitable for different situations, a non-compliant balloon may be useful to prevent the balloon 90 from expanding in the area where the side aperture is provided.

One concern regarding the use of angioplasty is restenosis. Restenosis, or the re-narrowing of the arteries, affects a percentage of patients receiving angioplasty. While the use of a stent in combination with the angioplasty has significantly reduced the occurrence, restenosis is still an issue. To address this potential problem it may be desirable to coat the stent with a pharmaceutical agent. While different pharmaceutical agents work differently, in an embodiment, the drug coating may be configured to provide an anti-restenotic or anti-neointimal proliferation effect. In an embodiment, the coating may be RAPAMYCIN or SIROLIMUS.

As can be appreciated from FIG. 8, using a standard stent in the junction 50 would be problematic. For example, in FIG. 8 if a standard stent was used, when the stent was expanded the passageway to the second branch 46 would be as least partially blocked.

Figure 9:
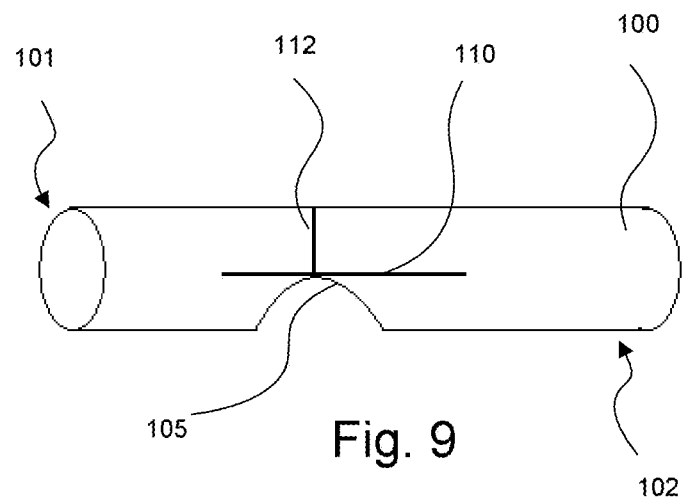
FIG. 9 illustrates a top view an embodiment of a stent in accordance with an aspect of the present invention.
Figure 10:
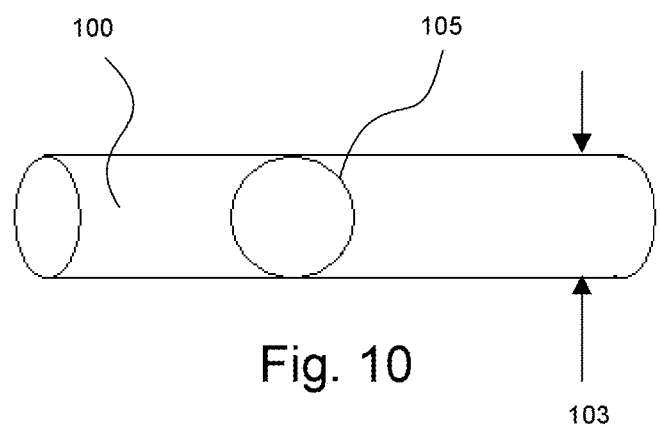
FIG. 10 illustrates a side view of the stent in FIG. 9 in accordance with an aspect of the present invention.

Looking at FIG. 9, an alternative to the normal stent is depicted as stent 100. The stent 100 has a proximal end 101, a distal end 102 and includes a side aperture 105, a first marker 112 and a second marker 110. The use of the markers will be discussed below. FIG. 10 illustrates a side view of the stent 100. As can be appreciated from FIGS. 9 and 10, the side aperture 105 is circular.

Figure 11:
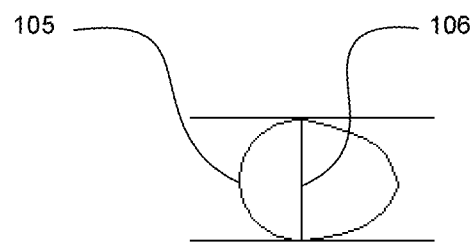
FIG. 11 illustrates a side aperture of a stent in accordance with an aspect of the present invention.

In an embodiment it may be desirable to provide a side aperture that is elongated on one side. FIG. 11 illustrates an embodiment of a side aperture 105 that includes a center line 106 and is elongated on one side of the center line 106.

Figure 22:
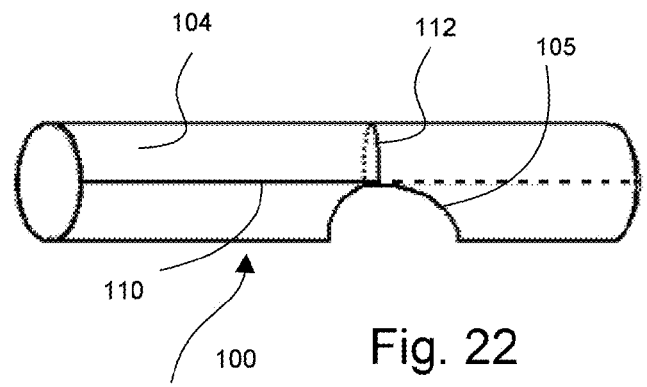
FIG. 22 illustrates a top view of an alternative embodiment of a stent in accordance with an aspect of the present invention.
Figure 23:
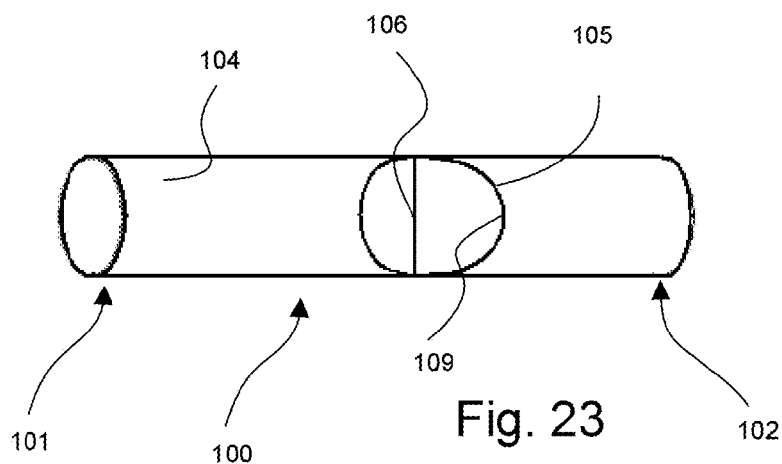
FIG. 23 illustrates a side view of the stent depicted in FIG. 22 in accordance with an aspect of the present invention.

Looking ahead to FIGS. 22 and 23, an alternative embodiment of a stent 100 is depicted. The stent 100 includes a proximal end 101 and a distal end 102. A cylinder wall 104 that opens at the proximal end 101 and the distal end 102 includes a side aperture 105. It should be noted that the cylinder wall 104 of the stent 100 is configured to allow the stent 100 to expand. Thus, the cylinder wall 104 may comprise any of the known wall designs used for expanding stents. As can be appreciated, the side aperture 105 is shown with a center line 106. It is noted that in practice the center line 106 would not be visible and is thus being provided as a reference for purpose of discussion. As depicted, the side aperture 105 is elongated on one side of the center line 106, thus making it more difficult to define the true center. For purpose of discussion, however, the center line 106 as used herein refers to an imaginary reference line on the side aperture 105 that the operator should attempt to align with the center of the second branch 46 (FIG. 3). As can be appreciated, as the center line 106 is an imaginary reference line that is not visible to the operator, the markers that may be provided on the stent 100 can aid the operator in performing the alignment process. Thus, the markers may aid the operator in effectively aligning the center line 106 with the side branch 46. It is noted that in an embodiment the first marker 112 may be aligned with the center line 106.

It should be noted that as depicted the side aperture 105 provides a relatively smooth edge 109 in the cylinder wall 104. While not required, this allows a second stent to be inserted through the side aperture 105 with less likelihood of snagging the stent 100 and moving it out of location or breaking off a piece of the stent 100. As can be appreciated, the occurrence of such events is difficult to detect but generally requires emergency surgery if detected in time, and therefore is undesirable. It should be noted that in an embodiment the size of the side aperture 105 may be substantially the same as the openings in the stent 100 at the proximal and distal ends 101, 102 so as to provide substantially the same effective lumen for each branch.

Referring to FIG. 22, a first marker 112, partially provided in dotted line, extends around a portion of the circumference of the stent 100. As can be appreciated, this configuration, while not required, is helpful in positioning the stent. As can be further appreciated, the stent includes a second marker 110 that has a first half on one side of top of the stent and a second half on the bottom of the stent 100. This allows the second marker 110 to effectively extend the length of the stent 100 while providing additional information to the operator during implantation of the stent. For example, if the viewing angle is properly aligned, the second marker 110 will appear to be a continuous line. Of course, in an alternative embodiment the second marker 110 may be a continuous line.

In an embodiment, the second marker 110 may be aligned with the longitudinal axis of the stent 100. In an alternative embodiment, the second marker 110 may be aligned parallel to the longitudinal axis of the stent 100. As can be appreciated, a parallel configuration may provide more precise feedback to the operator during implantation but requires additional manufacturing precision.

It should be noted that the first marker 112 may be positioned so as to be perpendicular to the second marker 110. While such a position is not required, if the second marker 110 is parallel to the longitudinal axis and the first marker 112 is perpendicular to the second marker 110, the position of the stent 100 can be more accurately determined prior to expansion of the stent 100.

Figure 24:
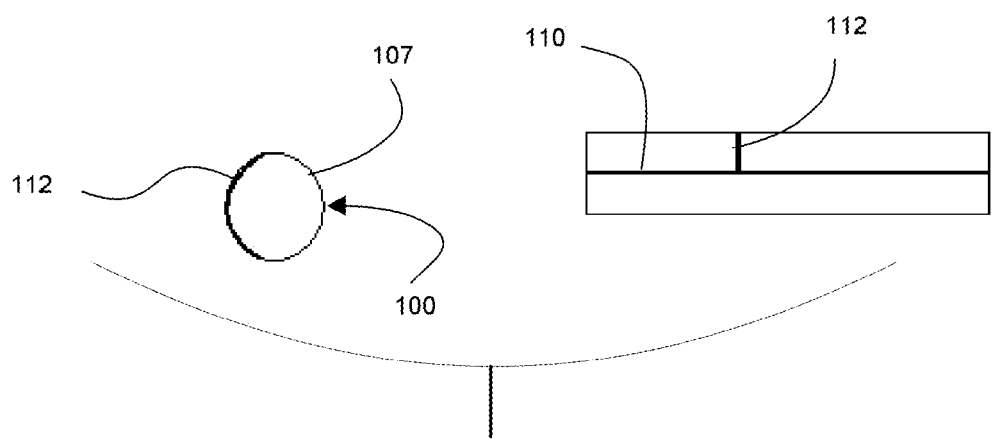
FIG. 24 depicts a stent in a compressed state in accordance with an aspect of the present invention.

In this regard, it should be noted that when the stent 100 is in the non-expanded state it is difficult to discern the location of the side aperture 105. Thus, the use of one or more markers that are visible while the stent 100 is still in the compressed state will tend to prevent the stent 100 from being expanded in an incorrect position. For example, as depicted in FIG. 24, a non-expanded stent 100 is shown in two views and at least one of the first marker 112 and the second marker 110 is/are visible on the compressed stent 100 in either view.

Figure 12:
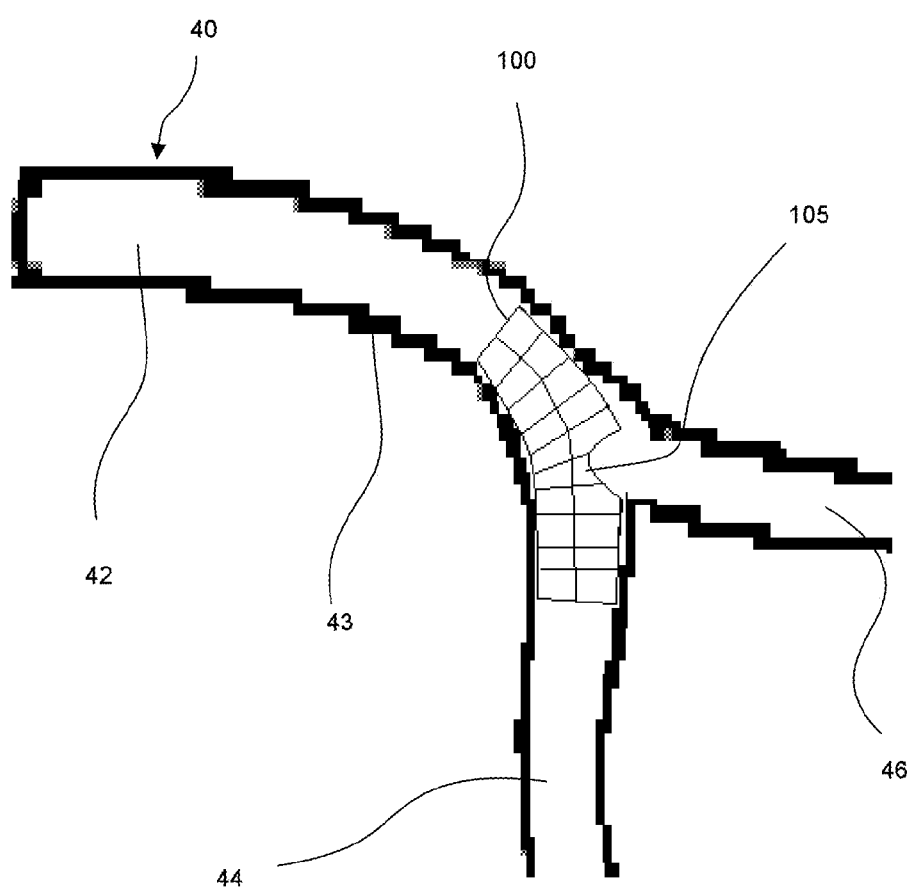
FIG. 12 illustrates a sectional view of an embodiment of a stent implanted in accordance with an aspect of the present invention.

Returning to FIG. 12, a left coronary artery 40 is depicted with the stent 100 supporting the wall 43 from the main branch 42 to the first branch 44. However, to avoid blocking the second branch 46, the side aperture 105 is aligned so as to allow blood to flow through the stent 100 into the second branch 46. As can be appreciated, when installed the wall 43 will be in contact with most of the stent 100; thus, the stent 100 will act as a support structure to help ensure that blood flow to the branches 44, 46 remains non-obstructed.

While in many situations it may be sufficient to implant the stent 100, in other circumstances, such as depicted in FIG. 6a, it may be beneficial to provide additional support for the wall 43. One way of doing so is to install a second stent. For example, a second stent extending from the side aperture 105 would provide a "Y" shaped support structure (FIG. 16) that could help ensure the blood continues to flow from the main branch 42 to the branches 44, 46.

Figure 13:
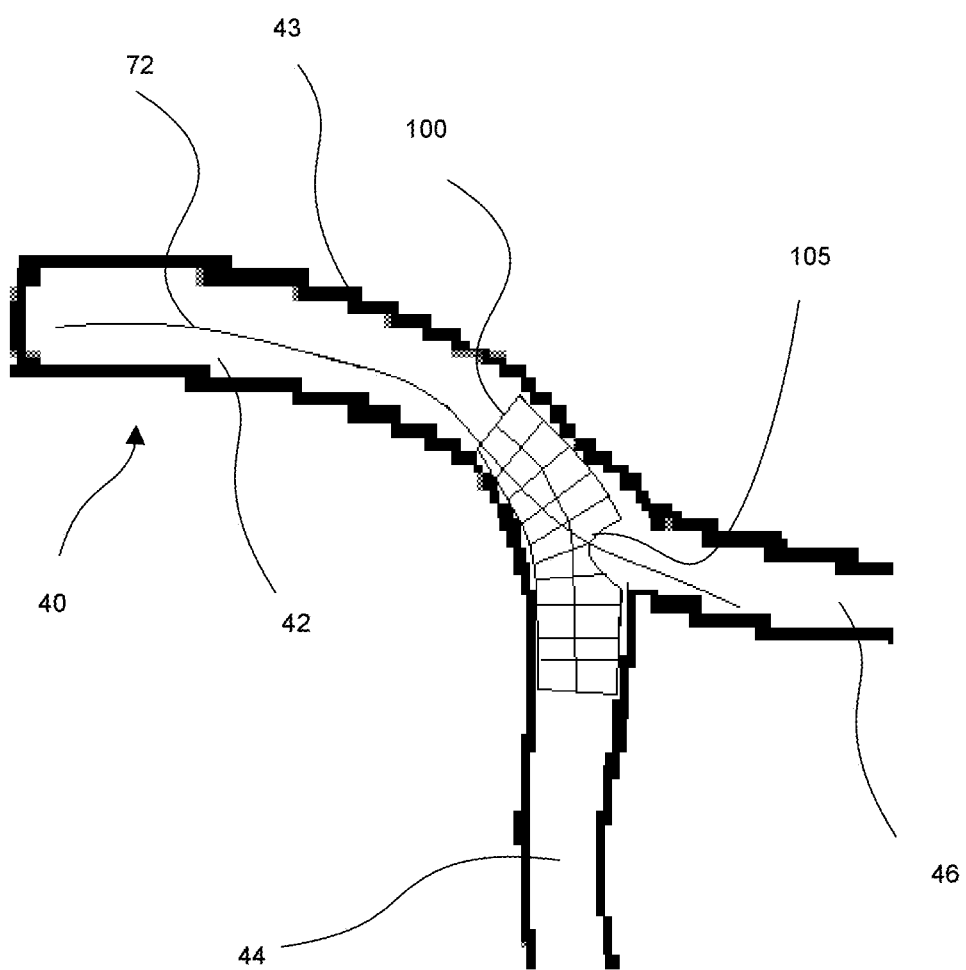
FIG. 13 illustrates a sectional view of an embodiment of a guide wire being inserted in accordance with an aspect of the present invention.

To provide the "Y" shaped structure, first, as depicted in FIG. 13, a guide wire 72 is inserted into the left coronary artery 40 and guided through the side aperture 105. This may be a different guide wire than the guide wire 70 or it may be the same guide wire. One potential issue with inserting a guide wire into the left coronary artery 40 after the stent 100 is implanted is that the guide wire 72 has a limited ability to bend and go around tight curves and could possibly catch on the stent 100. As previously discussed, in an embodiment the side aperture 105 may be elongated on one side. While not required, the elongated side aperture allows the guide wire 72 to be inserted into the second branch 46 while reducing the possibility that the guide wire might catch on the stent 100. In an alternative embodiment the side aperture 105 could simply be made larger.

Figure 14:
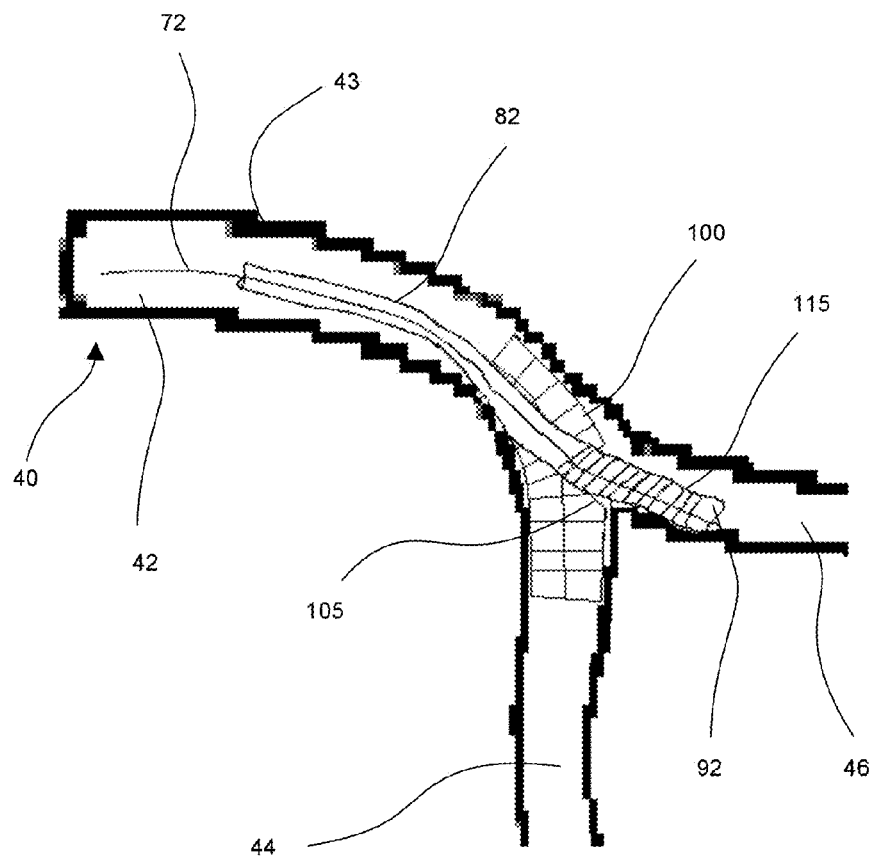
FIG. 14 illustrates a sectional view of an embodiment of a stent being implanted in accordance with an aspect of the present invention.

Once the guide wire 72 is inserted, a catheter 82 is inserted along the guide wire 72 until the balloon 92 is positioned as desired. In an embodiment, as depicted in FIG. 14, the balloon 92 extends out of the side aperture 105 and includes a stent 115 mounted to the outside of the balloon 92. In an embodiment the side aperture is elongated so that the balloon 92 and stent 115 pass through the side aperture 105 without catching on the stent 100. In an embodiment, when the stent 115 is expanded the stent 115 and stent 100 will have some overlap. In an alternative embodiment, the stent 115 will not overlap with the stent 100 but will be positioned via the side aperture 105. In another alternative embodiment, the stent 115 may be positioned first and then the stent 100 may be positioned so that the side aperture 105 aligns with the stent 115. To provide maximum support, however, it may be beneficial to have some overlap between the stent 100 and the stent 115.

Figure 15:
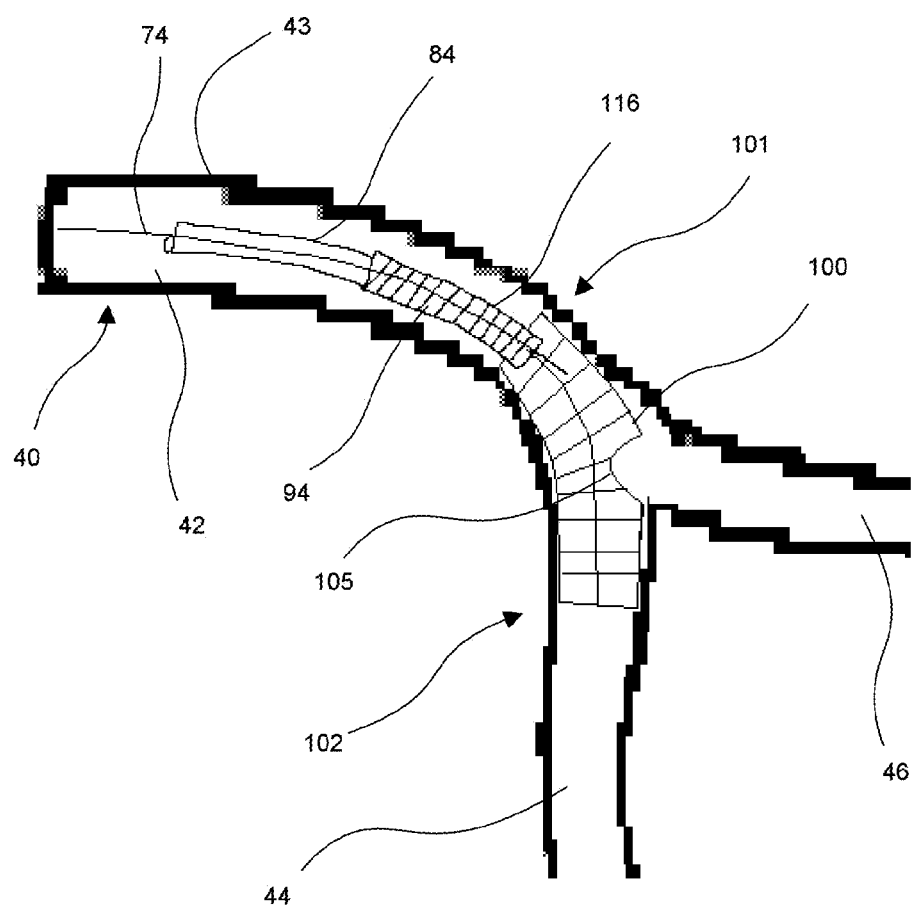
FIG. 15 illustrates a sectional view of an embodiment of a stent being implanted in accordance with an aspect of the present invention.

In an alternative embodiment, as depicted in FIG. 15, a guide wire 74 will be inserted past the proximal end 101 of the stent 100 and a catheter 84 with a balloon 94 will be inserted so that a portion of a stent 116 overlaps with the stent 100. The balloon 94 may then be inflated so that the stent 116 and stent 100 provide a more complex support structure. It should be noted that it may be useful to use a balloon 94 with a lesser degree of compliance so that the stent 116 is expanded in a uniform manner.

Figure 16:
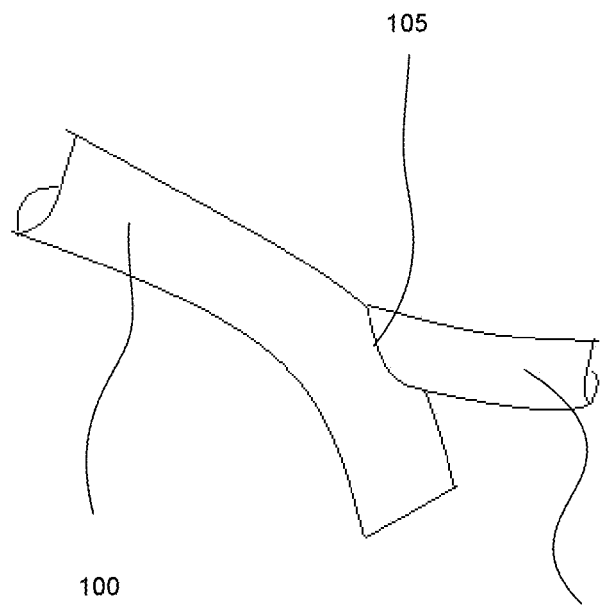
FIG. 16 illustrates an elevated view of an embodiment of a support structure created by two stents in accordance with an aspect of the present invention.
Figure 17:
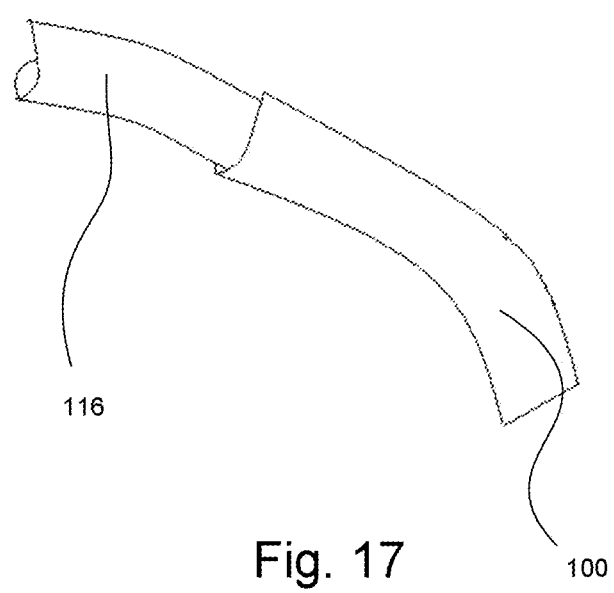
FIG. 17 illustrates an elevated view of an embodiment of a support structure created by two stents in accordance with an aspect of the present invention.

As illustrated in FIGS. 16 and 17, the stents 115, 116 are positioned and expanded to form a "Y" shaped support structure or an expanded tubular shaped support structure, respectively. In an embodiment, both the stent 115 and the stent 116 may be added to the stent 100 to maximize support of the left coronary artery 40. As can be appreciated, combinations of one or more stents 100, 115 and 116 may be used in an overlapping fashion; thus, a complex support structure is possible. It is expected, however, that one or two stents will typically be sufficient.

It should be noted that in an alternative embodiment the stent 115 may be a self-expanding stent. In such an embodiment, the stent 115 would be positioned and then allowed to expand. In an embodiment the self-expanding stent 115 would include one or more markers to allow the operator to more accurately determine where the proximal and/or distal ends are located.

As can be appreciated, the size of stent 100 may be adjusted as desired and used in other junction locations in different blood vessels. For example, the distance between the distal end 102 and the side aperture 105 may vary as desired. In addition, different locations may require an outer diameter 103 of the stent 100 (FIG. 10) to be adjusted so as to provide proper support for the wall of the blood vessel.

It should be noted that in an embodiment a stent 100 may be inserted after the balloon is expanded a first time. In such an embodiment, a first balloon would be expanded and then contracted. The first balloon would then be removed. Next the stent 100 would be installed. In such a scenario the stent 100 could be a self-expanding stent or a balloon expanded stent as discussed above. Thus, expanding a stent includes using a balloon to expand the stent or allowing the stent to self-expand. As the general procedure for inserting and expanding a stent in an artery is known to persons of skill in the art, additional details are not provided herein.

As can be appreciated, care must be used when positioning the stent 100 and the side aperture 105 and the optional stents 115, 116 or the support structure will not work as intended. For example, it is beneficial to align the side aperture 105 with the second branch 46 so as to avoid occlusion of the second branch 46.

In an embodiment, the stent may be made of a stainless steel alloy, although other materials may be used. It is noted that the type of stent is not crucial; thus, for example but without limitation, a coiled spring design, a slotted tube design or mesh design may be used. However, one potential issue with the insertion of stents is that under certain known viewing methodologies the stent will not be visible (e.g. the stent will be radiolucent). Even if the stent is not radiolucent, seeing the stent without being able to determine its orientation can make aligning the side aperture more difficult.

To allow for improved orientation of the stent, radioopaque markers may be included on the stent. In an embodiment the markers may include a gold coating; however, other coatings may also be used. Looking at FIG. 18, a stent 100 includes a first marker 112, a second marker 110, a third marker 113 and a fourth marker 114. In an embodiment, as depicted, the first marker 112 and the second marker 110 may be perpendicular in orientation. The third and fourth markers 113, 114 may be positioned on proximal end 101 and distal end 102 of the stent 100. In an embodiment, a stent may have one or more of the markers as is appropriate. As can be appreciated, other shapes of markers other than lines may also be used.

It should also be noted the first marker 112 may include several distinct symbols that together form the first marker 112. Thus, the term marker refers to a set of one or more symbols, and may be, for example and without limitation, a set of dots, a geometric shape or some other configurations that allows the operator to determine aspects of the orientation of the stent 100. An advantage of using a line, however, is the ease of viewing such a marker during implantation of the stent.

Figure 18:
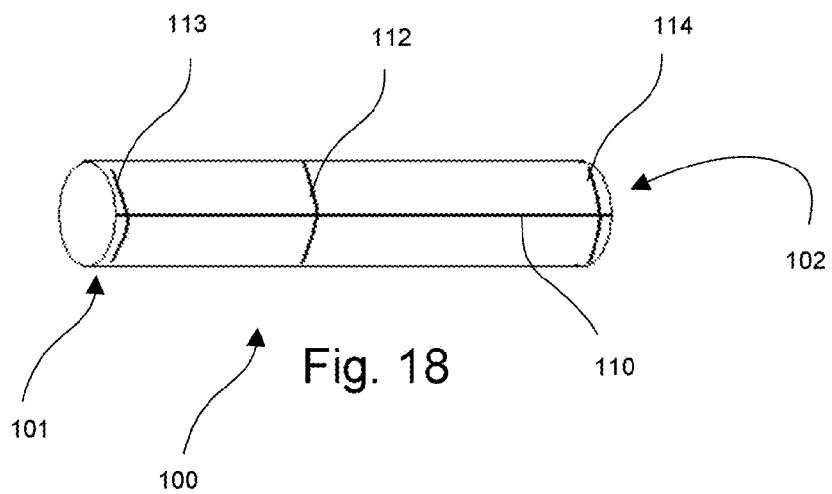
FIG. 18 illustrates an elevated view of an embodiment of a stent in accordance with an aspect of the present invention.
Figure 19:
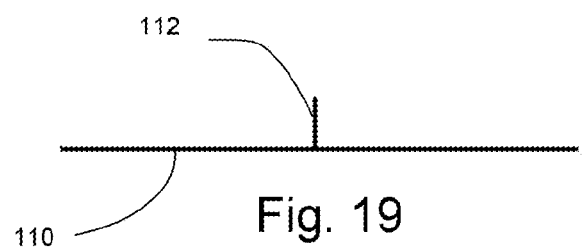
FIG. 19 illustrates an elevated view of an embodiment of two markers in accordance with an aspect of the present invention.
Figure 20:
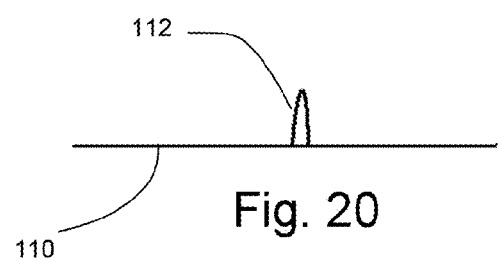
FIG. 20 illustrates an alternative elevated view of an embodiment of the two markers in FIG. 19 in accordance with an aspect of the present invention.

In an embodiment, the first marker 112 may extend around a radial portion of the stent 100 as depicted in FIG. 18. In an embodiment, the first marker 112 may extend around about half of the stent 100. While not required, the advantage of having the first marker 112 extend around about half of the stent 100 can be appreciated in light of FIGS. 19 and 20. If the orientation of the stent is aligned with the angle of viewing, the first marker 112 will look like a straight line, as illustrated in FIG. 19. If the orientation of the stent 100 is not aligned with the viewing angle, the first marker 112 will resemble the appearance of the first marker 112 in FIG. 20. As can be appreciated, this allows the operator positioning the stent 100 in the blood vessel to determine and/or verify the angular orientation of the stent 100.

Figure 21:
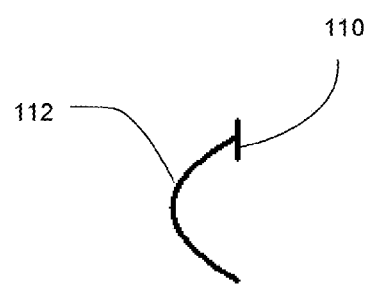
FIG. 21 illustrates an alternative elevated view of an embodiment of the two markers in FIG. 19 in accordance with an aspect of the present invention.

In addition to allowing the determination of angular orientation, configuring the stent 100 to include the first marker 112 with the first marker 112 being "C" shaped can also allow the operator to determine whether the rotational orientation of the stent is correct as illustrated by FIG. 21. Thus, the angular and rotational orientation may be determined with the first marker 112 so that the stent 100 is properly positioned before being expanded.

In an embodiment, the first marker 112 may be directly aligned with the centerline 106 (FIG. 23) of the side aperture 105. Thus, the operator positioning the stent 100 can line up the first marker 112 with the middle of the second branch 46 (FIG. 3) so as to maximize blood flow to the second branch 46. As can be appreciated, however, the first marker 112 may also be aligned with some other part of the side aperture 105.

In an embodiment, the first marker 112 may extend the length of the stent 100. While not required, such a configuration aids in the implantation of additional stents. For example, in an embodiment a support structure as depicted in FIG. 16 may be desired. To provide the depicted support, first the stent 100 with the side aperture 105 may be installed. The first and second markers 110, 112 allow the stent 100 to be properly orientated with respect to the second branch 46 before the stent 100 is expanded (FIGS. 8 and 9). In an embodiment the stent 115 may include the third and fourth markers 113, 114, which may be aligned with the proximal and distal ends of the stent 115, thus allowing the stent 115 to be aligned with respect to first and second markers 110, 112. Therefore, a stent 115 with the third and fourth markers 113, 114 may be positioned so as to partially extend from the side aperture 105 (FIG. 14).

If the support structure as depicted in FIG. 17 is desired, in an embodiment where the first marker 112 extended the length of the stent 100, the fourth marker 114 on the stent 115 could be positioned with respect to the first marker 112 on the stent 100. Thus, in an embodiment it could be determined when there was an overlap because the two markers 110, 114 would cross in a two-dimensional view. It should be noted that the same stent 115 may be used in either configurations shown in FIGS. 16 and 17. In an alternative embodiment, however, a different stent may be used. The advantage of using the same stent to obtain either the structure in FIG. 16 or FIG. 17 is a reduced number of parts, thus reducing the chance that the wrong stent will be used. However, having a variety of different sized stents may allow for a more precise fit if such a fit is found to be useful for a particular patient. For example, the secondary branch might be much smaller than the main branch and thus would benefit from a stent with a smaller outer diameter.

Figure 25A:
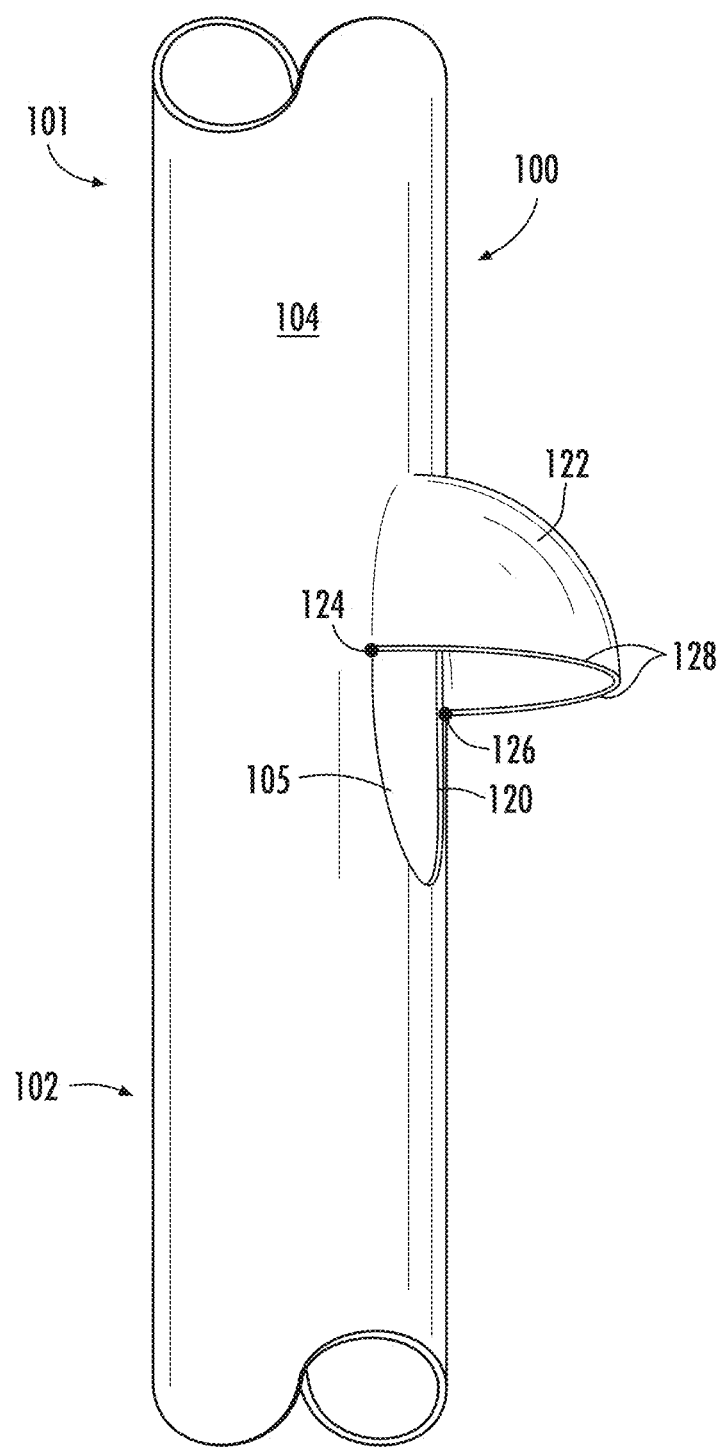
FIG. 25A shows a perspective side view of the exemplary stent and FIG. 25B shows a top view of the exemplary stent.
Figure 25B:
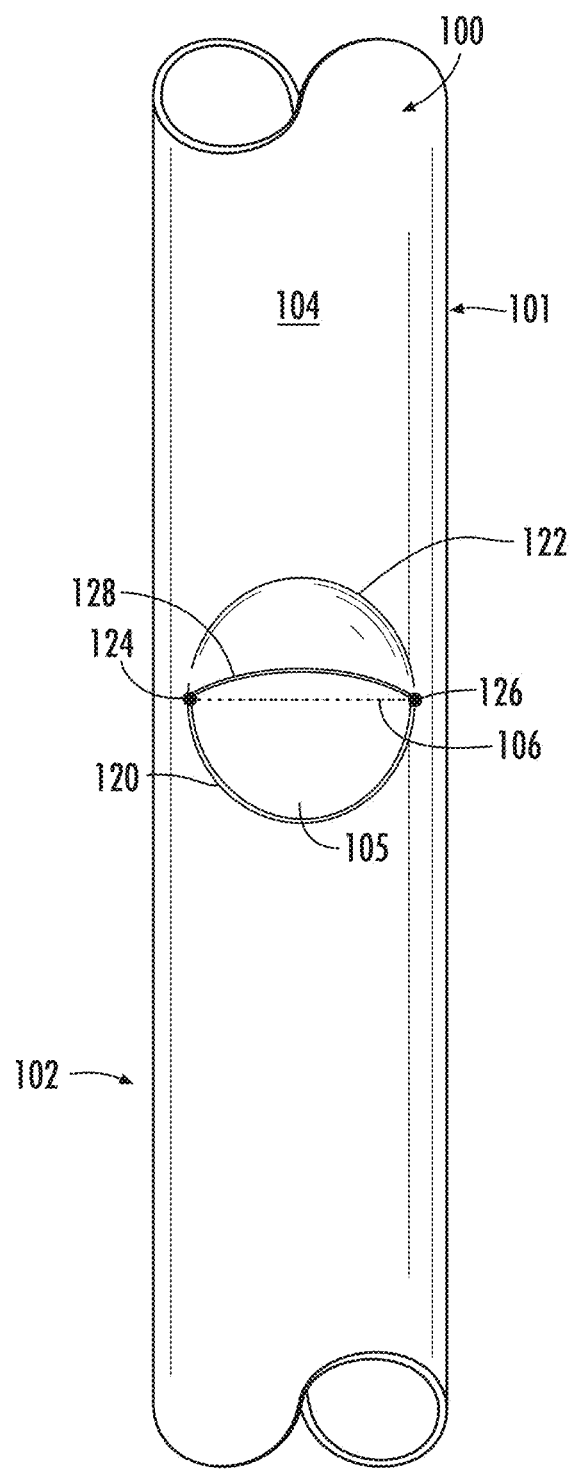

FIGS. 25A and 25B show an exemplary stent 100 according to one embodiment of the invention. Specifically, FIG. 25A shows a perspective side view of stent 100 and FIG. 25B shows a top view of exemplary stent 100. As shown in FIGS. 25A and 25B, exemplary stent 100 includes a proximal end 101 and a distal end 102. A cylinder wall 104 that opens at the proximal end 101 and the distal end 102 includes a side aperture 105. Exemplary aperture 105 is shown to be substantially circular, however, those skilled in the art will realize that, similar to other embodiments described herein, the aperture 105 is not required to be circular, but may assume any other shape, simple or complex, having a perimeter. In certain embodiments, the cylinder wall 104 of the stent 100 is configured to allow the stent 100 to expand. The cylinder wall 104 may comprise any of the known wall designs used for expanding stents.

As shown in FIG. 25B, the side aperture 105 is shown with a center line 106. It is noted that in practice the center line 106 would not be visible and is thus being provided as a reference for purpose of discussion. In certain embodiments, the side aperture 105 may be elongated on one side of the center line 106, thus making it more difficult to define the true center. For purpose of discussion, however, the center line 106 as used herein refers to an imaginary reference line on the side aperture 105 that the operator should attempt to align substantially with the center of a second branch 46 (FIG. 3).

Side aperture 105 is defined by perimeter 120. It should be noted that as depicted, aperture 105 provides a relatively smooth edge in the cylinder wall 104. While not required, this may assist, in some embodiments, the insertion of a second stent through the side aperture 105 with less likelihood of snagging the stent 100 and moving it out of location or breaking off a piece of the stent 100. As can be appreciated, the occurrence of such events is difficult to detect but generally requires emergency surgery, and therefore is undesirable. It should be noted that in an embodiment, the size of the side aperture 105 may be substantially the same as the openings in the stent 100 at the proximal and distal ends 101, 102 so as to provide substantially the same effective lumen for each branch.

Further aspects of the invention relate to stents having an extension and methods for using novel stents with an extension. As shown in both FIGS. 25A and 25B, stent 100 comprises an extension 122 that extends from a portion of the perimeter 120 of the aperture 105. Extension 122 may comprise one or more biocompatible substances and/or pharmaceutical agents. In one embodiment, extension 122 is substantially the same composition as stent 100. As shown best in FIG. 25B, extension 122 extends from the perimeter 120 in a substantially continuous form. For example, exemplary extension 122 extends around perimeter 120 between points 124 and 126. As used herein, "substantially continuous" means without any substantial breakage. For example, extension 122 may have perforations and/or areas of decreased thickness to assist in expansion and/or flexing of the extension 122, however, any such areas are configured to minimize or prevent any flow of fluids through those areas rather than through the pathway created by the aperture 105.

As shown in FIG. 25B, points 124 and 126 are located at about a midline of the perimeter, thus in the illustrated embodiment, extension 122 extends around approximately 50% of the perimeter. In yet other embodiments, extension 122 may extend less than about 50%. In certain embodiments, the extension 122 extends approximately 30-40% of the perimeter 120. In certain embodiments, the extension may extend at least about 25% of the perimeter 120. In certain embodiments, the extension 122 extends approximately 20-75% of the perimeter 120. In other embodiments, extension 122 may extend more than about 95% of the perimeter. For example, on one side, extension 122 may extend a first distance away from the stent's cylinder wall 104, while on a second side, extension 122 may extend a second distance away from the stents cylinder wall 104, in which the first distance is visually shorter than the second distance, when viewed during the implantation procedure using conventional imaging equipment. Further, as shown in FIGS. 25A and 25B, the extension 122 may be shaped as to have a longitudinal axis that is neither directly parallel nor perpendicular with the longitudinal axis of the cylinder wall.

In certain embodiments, extension 122 is configured to extend outward from the cylinder wall 104 and form a hood-like protrusion that arches over the perimeter 122. As used herein, "hood-like" refers to an extension that, if viewed from directly over and aligned with the center of the perimeter 120 (i.e., perpendicular to the center of midline 106 shown in FIG. 25B), the extension 122 would appear to cover at least a portion of the area within perimeter 120. In one embodiment, the extension may extend cover about 10% of area within perimeter 120. In certain embodiments, the extension may extend at least about 25% of area within perimeter 120. In certain embodiments, the extension 122 may cover approximately 30-40% of the area within perimeter 120. In certain embodiments, the extension 122 may cover approximately 20-75% of the area within perimeter 120.

Those skilled in the art will appreciate that the extent to which the extension 122 extends over (and thus cover the area within) perimeter 120 depends on one or more factors, including for example, the intended implantation site of stent 100. Furthermore, in certain embodiments, the stent is configured to be flexible, such that without pressure from, for example, being implanted in a branch, it is designed to flex to a certain position, however, upon being implanted, may flex to a second position. Thus, in one embodiment, extension 122 may be configured to cover about 10% of the area within perimeter 120, however, upon implantation, flexes to cover more than 10% of the area within perimeter 120.

In the exemplary embodiment shown in FIGS. 25A and 25B, edge 128 of extension 122 arches over the perimeter in a latitudinal direction that is perpendicular to the longitudinal axis of the cylinder wall 104. Specifically, edge 128 of extension 122 is shown to extend in a substantially latitudinal direction at the location where the distance of the aperture along the latitudinal direction is the greatest. (e.g., midline 106, shown in FIG. 25B). Those skilled in the art will readily appreciate, however, that the arch is not required to be located in a substantially latitudinal direction. In certain embodiments, edge 128 may arch is a substantially longitudinal direction (e.g. if extension 122 was rotated about 90 degrees to the right or to the left). In other embodiments, extension 122 may be off-axis with respect to the latitudinal and longitudinal directions as shown in FIGS. 25 and 25B. Moreover, as discussed above, edge 128 is not required to extend over the perimeter 122 at about midline 106.

Figure 26A:
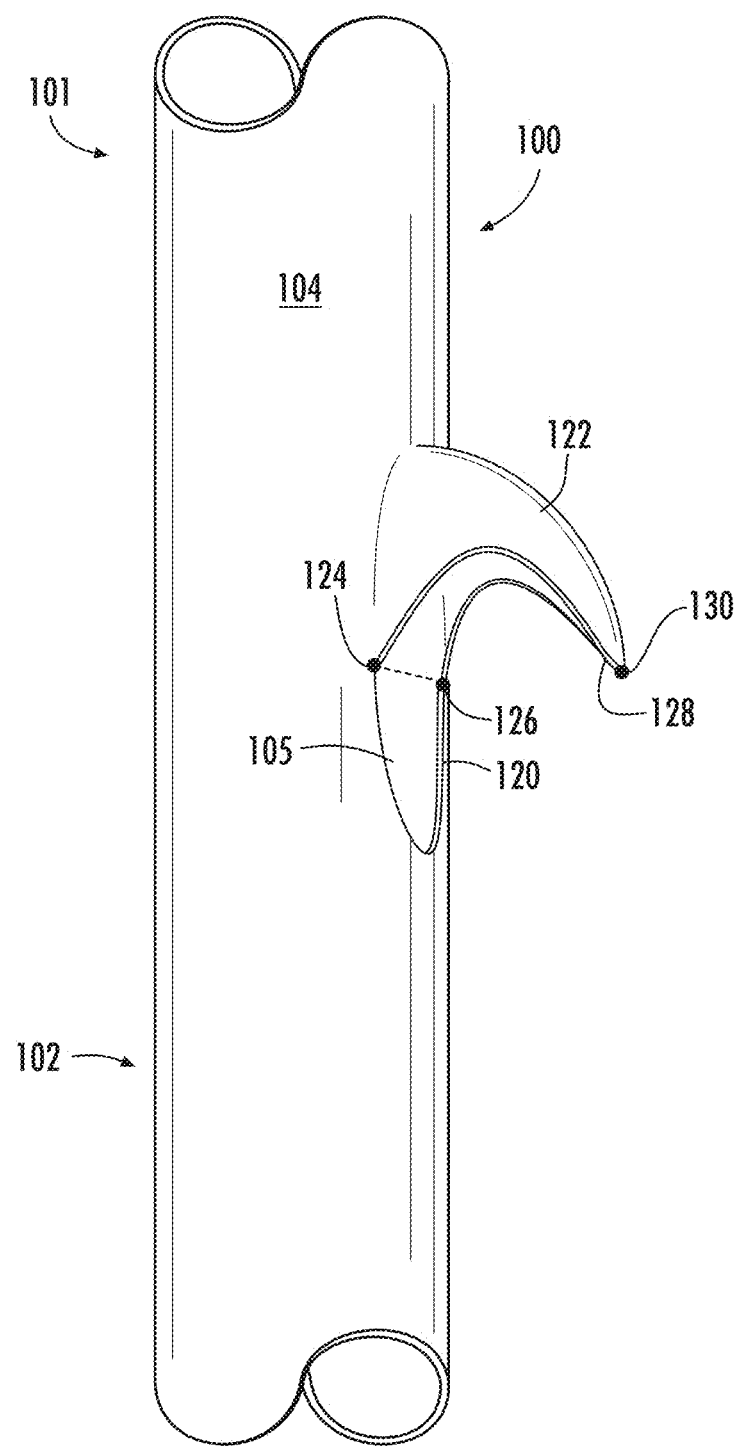
FIG. 26A shows a perspective side view of the exemplary stent and FIG. 26B shows a top view of the exemplary stent.
Figure 26B:
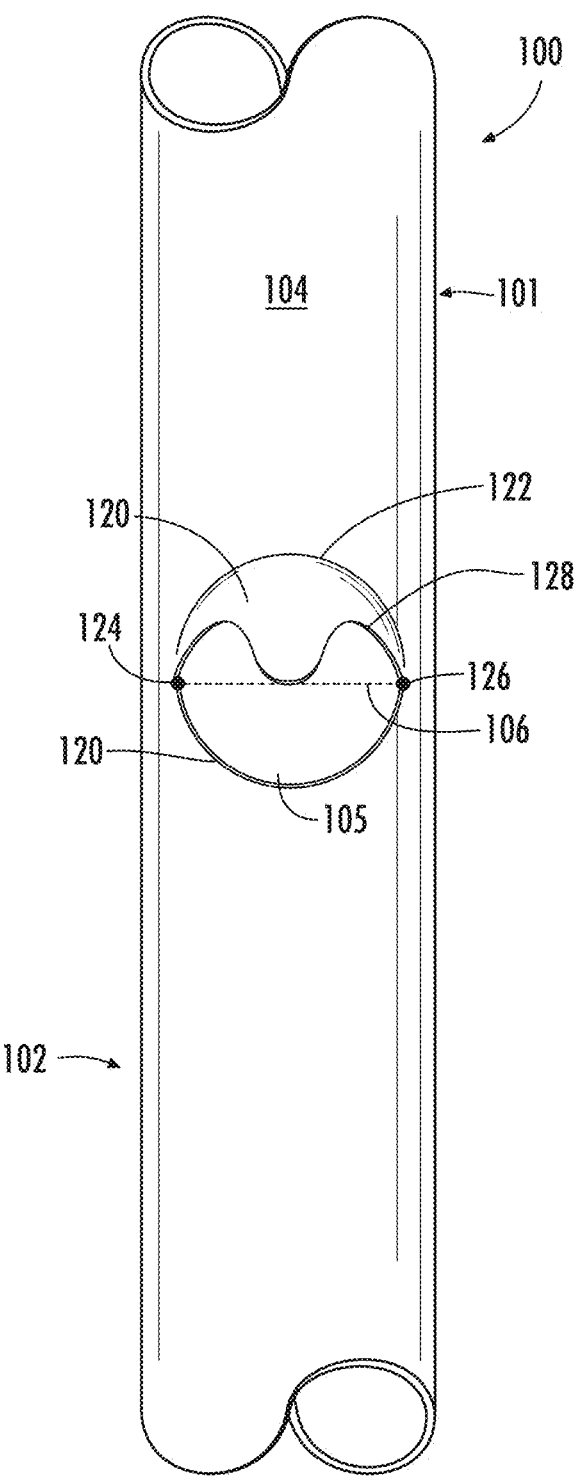

FIG. 26A shows a perspective side view of stent 100 and FIG. 26B shows a top view of exemplary stent 100. Similar to the embodiment displayed in FIGS. 25A and 25B, the embodiments shown in FIGS. 26A and 26B depict an extension 122 that is configured to extend outward from the cylinder wall 104 and form a hood-like protrusion that arches over the perimeter 120. Edge 128 of FIGS. 26A and 26B, however, are not straight, rather edge 128 initiates at about points 124 and 126 and extends in a wave like fashion, first extending away from the midline 106 and subsequently back towards the midline 106 as the hood-like extension 122. For example, in the illustrated embodiment, point 130 represents the furthest distance the exemplary extension 122 extends away from the perimeter 120 of the aperture 105 (i.e., similar to an apex of an arch). Thus, as shown in FIGS. 26A and 26B, edge 128 (and/or any resulting arching structure) is not required to be straight.

While the exemplary embodiment of FIGS. 26A and 26B shows point 130 as being substantially directly over midline 106, those skilled in the art will appreciate that this is just one embodiment, and point 130, while over a portion of the perimeter 120, is not required to be positioned at about a midline 130. Moreover, those skilled in the art will also appreciate that there are several other shapes and/or configurations for the arching behavior of edge 128, including but not limited to: adjusting flexibility/rigidity, tools and/or processes used to implant the stent 100, specific conditions of the patient the stent may be implanted within, and others. (Exemplary methods for implantation were discussed above and additional methods are discussed below).

Figure 27:
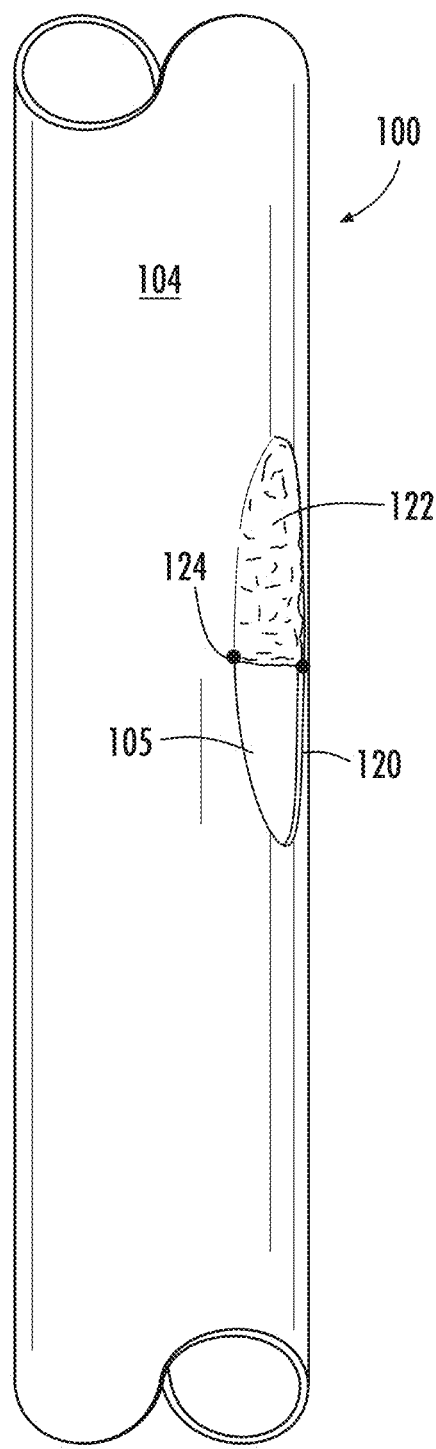
FIG. 27 shows a perspective side view of an exemplary stent with an extension in accordance with one embodiment of the invention.

In one embodiment, extension 122 may be flexible to expand from a first position to a second position. FIG. 27 shows a perspective side view of an exemplary stent 100 according to one embodiment of the invention. Looking to FIG. 27, stent 100 comprises an extension 122 in a first position. As seen, extension 122 is substantially within perimeter 120 of aperture 105. As used herein, substantially within means that extension 122 does not extend out of aperture 105 in a manner that would adversely affect insertion and/or implantation of the stent 100 into a patient. Extension 122 may expand to a second state upon an event or under predefined criteria. In certain embodiments, extension 122 may be configured to flex outward from the cylinder wall 104 upon expansion of the stent 100. For example, upon being expanded to the second state, the extension 122 may form a form a hood-like protrusion that over the perimeter 120 (e.g. as shown in FIGS. 25A, 25B, 26A and/or 26B).

In one embodiment, a partially-compliant balloon may be utilized to expand cylinder wall 104 and extension 122. In one embodiment, a partially-complaint balloon is positioned within a stent with a compliant portion of the balloon being positioned about the extension 122. Upon expanding the balloon, a non-compliant portion of the balloon may expand the cylinder body 104, however, a compliant portion of the balloon may expand further than the non-compliant portion of the balloon and, therefore, expand extension 122 from the first state to the second state. In other embodiments, expansion of the stent 100, alone, may not automatically trigger expansion of the extension 122 to a second state. Other events that may trigger the expansion of the extension 122 from the first state the second state, include but may not be limited to: using the same or another balloon to expand extension 122 to the second state after the cylinder body 104 has been expanded.

FIG. 28 shows an exemplary stent 100 upon being implanted in a patient. In one embodiment, extension 122 has been extended from a first state (e.g. as shown in FIG. 27) and is shown in the second state. FIG. 28 shows implantation of the stent 100 in the left coronary artery; however, those skilled in the art will appreciate that stents in accordance with one or more embodiments disclosed herein may be used in one or more other vessels within a body (human or non-human). As shown, the left coronary artery 40 is shown in an enlarged view that includes the left main artery or main branch 42 that feeds a first branch 44 (which as depicted is the left anterior descending artery) and a second branch 46 (which as depicted is the left circumflex artery). As can be further appreciated, the main branch 42 includes a wall 43. In order for blood to flow through the left coronary artery 40, the wall 43 forms a tube-like shape that preferably is free from blockage.

In one embodiment, a method may be employed that positions stent 100 to have aperture 105 in the junction of the first branch 43 and the second branch 44. As seen, aperture 105 extends along a longitudinal direction and along a latitudinal direction to form a perimeter 120. In one embodiment, stent 100 may include marker 132 which may be aligned with the side aperture 105 at a location the first marker is in-line with and directly extends from the location where the distance of the aperture along the latitudinal direction is the greatest, the first marker extending along a circumference of the stent a distance substantially perpendicular to a longitudinal axis of the stent so as to provide a rotational orientation of the stent in a two dimensional image.

Those skilled in the art will readily appreciate that marker 132, and/or other markers, may not be apparent or properly viewed in a collapsed stent, such as before the stent 100 is expanded in those embodiments where stent 100 is expandable from a first state to a second state. In this regard, embodiments of the invention relate to an expanding stent (i.e, so as to support the wall of the main branch and the first branch), whereby the side aperture allows the main branch 43 to continue to feed both the first branch 44 and the second branch 46. In further embodiments, the extension 122 may be flexible as to be expandable from a first state (e.g., as shown in FIG. 27) to a second state (e.g., shown in FIGS. 25-26 and/or 28). In one embodiment, extension 122 may be extended to be in a substantially continuous form from a portion of the side aperture's 105 perimeter 120 that flexes outward from the cylinder wall 104 to form a protrusion that arches in a direction over the perimeter 120 and extending into the second branch 46. As shown, extension 122 extends in a direction that is substantially aligned with the longitudinal axis (shown as dotted lines 134) of the second branch 46. In the exemplary embodiment, edge 128 of extension 122 is substantially parallel to the longitudinal axis 134 of the second branch 46. As discussed above, however, there is no requirement that edge 128 be directly parallel to any axis, but rather may include one or more curving structures.

In one embodiment, the extension 122 expands as a result of the expansion of the stent 100. As discussed above, one or more other events, actions, and/or predefined criteria may have to be met for the expansion of an extension from a first state to a second state. In one embodiment, the expansion of the extension 122 may occur after the expansion of the stent 100.

Figure 29A:
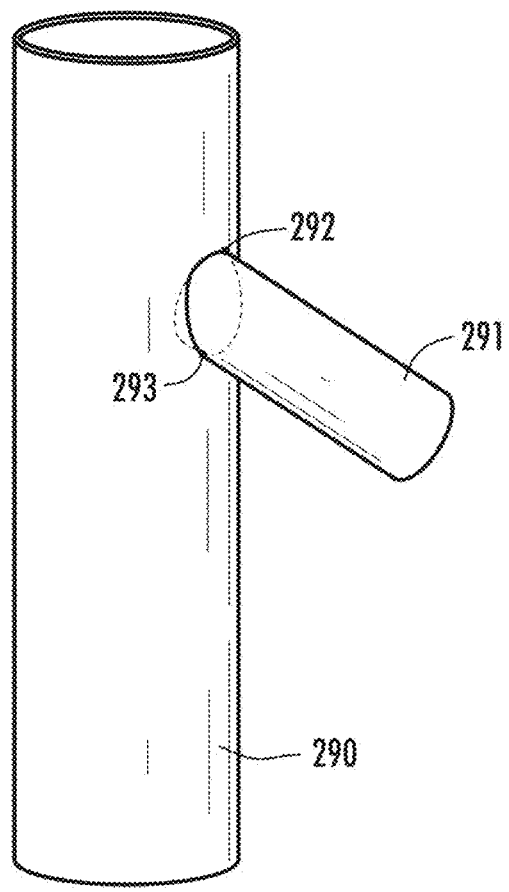
FIG. 29A shows a perspective view of a first support structure and FIG. 29B shows a perspective view of a second support structure.

Use of the novel stent 100 may overcome one or more shortcoming in the art. As one example, various procedures require the implantation of multiple stents in a single location. Often two or more stents are joined together. Looking to FIGS. 29A and 29B, stent 290 is generally in the shape of a cylindrical body. Stent 291 is connected to stent 290. As seen in FIG. 29A, stent 291 is connected to stent 290 at an angle, and thus, a portion of stent 292 (which is represented by the dotted lines) is within stent 290. For example, point 292 is located at about the junction where stents 290 and 291 meet. At point 292 any insertion of stent 291 within 290 is minimal, however, looking to point 293, it is within stent 290, and as such may slow the passage of any fluids within stent 290. Those skilled in the art will readily appreciate that blocking bodily fluids, whether blood or waste products, can lead to dangerous and lethal consequences.

Figure 29B:
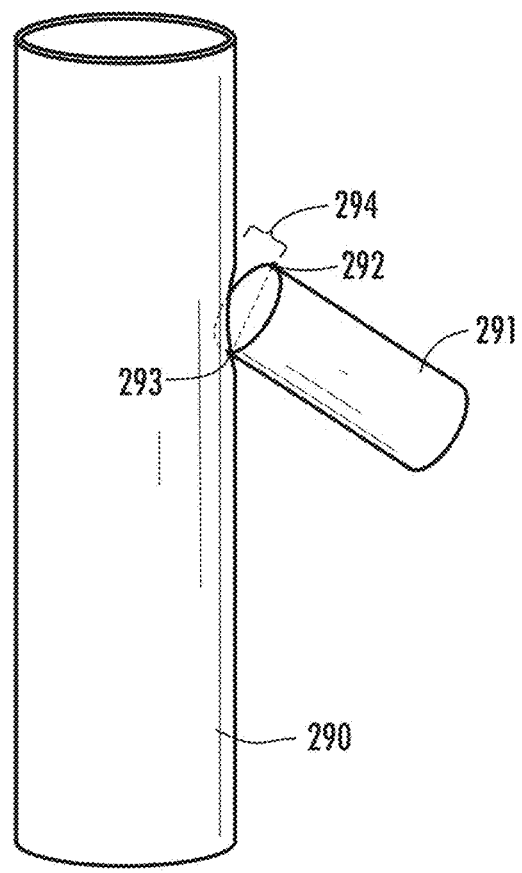

Conversely, FIG. 29B shows an embodiment where stent 291 is not substantially within stent 290. For example, point 203 is located at about the junction where stents 290 and 290 meet. In this instance, however, point 292 is no longer at the junction. Rather gap 294 is created between the stents 290, 291. This may result in undesired growth or collection of matter between the two stents. Further, it may lead to inadequate support at the juncture. In accordance with certain aspects of the invention, implementing extension 122 on either stent 290 and/or stent 291, may minimize or negate the problems associated with the arrangement of FIG. 29A and FIG. 29B. In this regard, certain embodiments of extension 122 may be configured to receive a second stent. Alternatively, in other embodiments, extension 122 may be configured to be received a by a second stent.

Figure 30A:
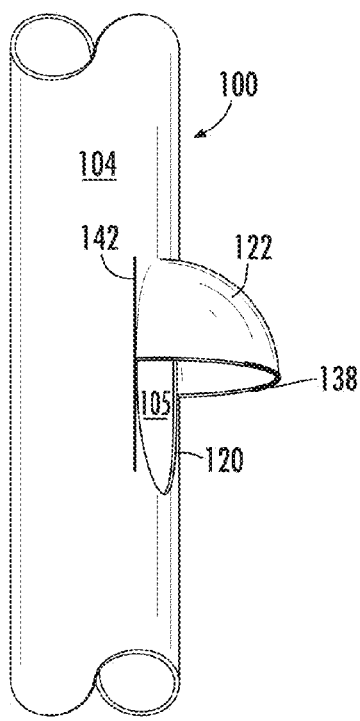
FIG. 30A shows a perspective side view of the exemplary stent and FIG. 30B shows a top view of the exemplary stent.
Figure 31A:
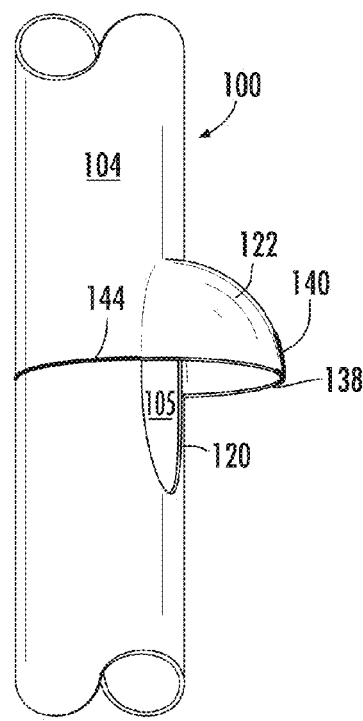
FIG. 31A shows a perspective side view of the exemplary stent and FIG. 31B shows a top view of the exemplary stent.
Figure 30B:
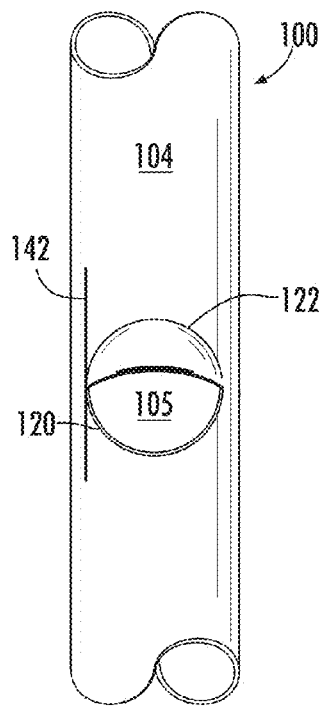
Figure 31B:
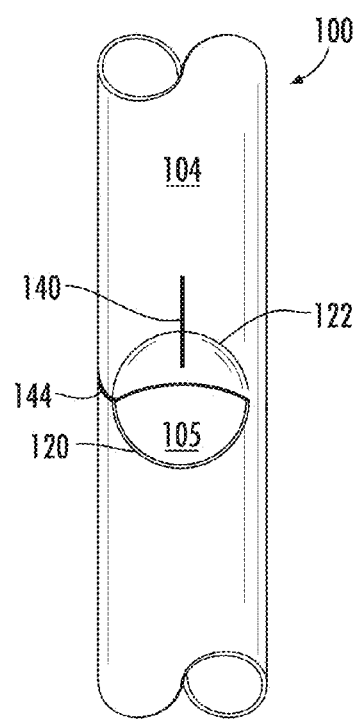

Further aspects relate to one or more markers being located on the extension 122. FIGS. 30-31 show exemplary stents having one or more markers on an extension in accordance with various embodiments. Looking first to FIGS. 30A and 30B, stent 100 comprises extension 122. As shown, marker 138 on the extension 122 arches substantially in a latitudinal direction over the perimeter in a direction that is substantially perpendicular to a longitudinal axis of the cylinder wall 104 of the stent 100. As shown, marker 138 is approximately located on edge 128. In one embodiment, marker 138 extends a distance to permit the capture of a rotation orientation of the extension in a dimensional image. In certain embodiments, marker 138 may not be entirely or even partially perpendicular to the longitudinal axis of the cylinder wall 104. For example, in embodiments, for example as shown in FIGS. 26A and 26B, edge 128 may not be straight, and as such in such embodiments in which marker 138 marks the edge 128, the marker 138 may not follow a straight path.

As appreciated by those skilled in the art, if extension 122 was rotated approximately 90 degrees to the right or to the left, marker 138 would be substantially parallel with (and in some embodiments, directly in line with) the longitudinal axis of the cylinder wall 104 of stent 100. Thus, in this illustrated embodiment and in others, marker 138 may be in line with either the longitudinal axis or the latitudinal axis of the cylinder wall 104. In this regard, marker 138 may have more than two components, and thus be parallel with (and possibly also inline with) the longitudinal and/or the latitudinal axis of the cylinder wall 104. Looking to FIGS. 31A and 31B, for example, marker 140 is substantially parallel with the longitudinal axis of cylinder wall 104. In this illustrated embodiment, marker 140 is also directly inline with the longitudinal axis of the cylinder wall 104 (best seen in FIG. 31B). In one embodiment, marker 138 and/or marker 140 may be positioned to traverse the location at which the extension 122 is furthest away from the aperture 105. In one embodiment, marker 138 may comprise an arch across the furthest point away from the side aperture 105.

In certain embodiments, one or more markers are configured so as to appear substantially perpendicular to each other in a two dimensional image. In certain embodiments, extension 122 may comprise a marker and the cylinder wall 104 of the stent 101 may comprise a marker. Looking again to FIGS. 30A and 30B, cylinder wall 104 may also comprise one or more markers. Marker 142, for example, is positioned adjacent the side aperture 105. In certain embodiments, marker 142 may extend a distance at least equal to a greatest longitudinal distance (as referenced from the cylinder wall 104) of the side aperture 105. In other embodiments, marker 142 may be shorter than the distance of the aperture, however, marks the location where the extension 122 meets the cylinder body 104, point 130 (shown in FIGS. 26A and 26B) and/or any other location on the extension 122.

Looking again to FIGS. 31A and 31B, stent 101 may comprise a marker (such as marker 144) that is positioned in-line with and directly extending from the location where the distance of the aperture 105 along the latitudinal direction (as referenced from the cylinder wall 104) is the greatest. In one embodiment, marker 144 may extend a portion of a distance around the circumference of the cylinder wall 104 in a direction extending away from the side aperture 105 and substantially perpendicular to a longitudinal axis of the cylinder wall 104 so as to provide a rotation orientation of the stent in a two-dimensional image. In one embodiment, marker 144 is directly aligned with a centerline of the side aperture 105. In one embodiment, marker 144 may extend entirely around the cylinder wall 104 and terminate at about the other side of the aperture 105. In one embodiment, marker 140 may creates an arch across the furthest point away from the aperture 105.

The present invention has been described in terms of preferred and exemplary embodiments thereof. Numerous other embodiments, modifications and variations within the scope and spirit of the appended claims will occur to persons of ordinary skill in the art from a review of this disclosure.

I claim:

1. A stent system configured to support a wall of at least one junction of a bodily vessel, the junction comprising a main branch, a first branch and a second branch, comprising:
    a stent having a cylinder wall configured to be expanded from a first state to a second state, wherein at the first state, the cylinder wall comprises a first circumference along a length extending from a first end to a second end along a first axis, a side aperture located at a fixed position with respect to the first and the second ends having a perimeter, and a flexible extension positioned substantially within the circumference; and
    wherein at the second state, the cylinder wall is configured to expand along its length configured to support the wall of the main branch and the first branch, to form a second circumference, wherein the second circumference is variable along the length of the cylinder and the flexible extension is configured to extend from a predefined portion of the side aperture's perimeter that, upon expansion of the stent, is configured to flex outward from the cylinder wall to form a hood-like protrusion that arches over the perimeter; and
    a first marker that upon expansion of the stent, is positioned in-line with and directly extending from a location where the distance of the aperture along the latitudinal direction is the greatest.

2. The stent system of claim 1, further comprising a second marker positioned on the flexible extension, wherein the second marker arches in a latitudinal direction over the perimeter in a direction that is substantially perpendicular to a longitudinal axis of the stent so as to provide a rotation orientation of the extension in a two-dimensional image.

3. The stent system of claim 1, wherein the stent is a first stent, the system further comprising a second stent configured to be at least partially positioned through the side aperture of the first stent.

4. The stent system of claim 3, wherein the second stent is configured to be expanded upon being partially positioned through the first stent, whereby the first and second stent form a support structure.

5. The stent system of claim 1, wherein the side aperture is a first side aperture, the stent comprising a second side aperture.

6. The stent system of claim 5, wherein the first side aperture and the second side aperture comprise a same diameter.

7. The stent system of claim 1, further comprising a second marker positioned on the flexible extension that forms an arch across the furthest point away from the aperture.

8. The stent system of claim 1, wherein cylinder wall includes a wall structure, the wall structure selected from the group consisting of a mesh design, a coil spring design and a slotted tube design.

9. The stent system of claim 1, wherein the stent is a mesh-type stent and the stent is coated with an anti-neointimal proliferation agent.

10. The stent of claim 1, further comprising a second marker positioned on the flexible extension that forms an arch across the furthest point away from the aperture of the first stent.

11. A stent system configured to support a wall of at least one junction of a bodily vessel, the junction comprising a main branch, a first branch and a second branch, comprising:
    a first stent having a cylinder wall configured to be expanded from a first state to a second state, wherein at the first state, the cylinder wall comprises a first circumference along a length extending from a first end to a second end along a first axis, a first side aperture located at a fixed position with respect to the first and the second ends having a first perimeter, and a flexible extension positioned substantially within the circumference;
    a second stent having a cylinder wall configured to be expanded from a first state to a second state; wherein at the second state, the cylinder wall of the first stent is configured to expand along its length configured to support the wall of the main branch and the first branch, to form a second circumference, wherein the second circumference and the flexible extension is configured to extend from a predefined portion of the side aperture's perimeter that, upon expansion of the stent, is configured to flex outward from the cylinder wall to form a hood-like protrusion that arches over the perimeter; and
    a first marker that upon expansion of the first stent, is positioned in-line with and directly extending from a location where the distance of the aperture along the latitudinal direction is the greatest.

12. The stent system of claim 11, wherein when the first stent is at the second state, its circumference is variable along the length of its cylinder wall.

13. The stent system of claim 11, wherein the second stent is configured to be at least partially positioned through the side aperture of the first stent when the second stent is at the first state.

14. The stent system of claim 13, wherein the second stent is configured to be expanded to the second state upon being partially positioned through the first stent, whereby the first and second stent form a support structure.

15. The stent system of claim 11, wherein the marker extends a portion of a distance around the circumference of the cylinder wall in a direction extending away from the side aperture and substantially perpendicular to a longitudinal axis of the stent so as to provide a rotation orientation of the stent in a two-dimensional image.

16. The stent system of claim 11, further comprising a second marker positioned on the flexible extension, wherein the second marker arches in a latitudinal direction over the perimeter in a direction that is substantially perpendicular to a longitudinal axis of the stent so as to provide a rotation orientation of the extension in a two-dimensional image.

17. The stent system of claim 11, wherein at the second state, the cylinder wall of the first stent is variable along the length of the cylinder wall.

18. The stent system of claim 11, wherein the first stent comprises a second side aperture.

19. The stent of claim 18, wherein the first side aperture and the second side aperture comprise a same diameter.

* * * * *